(12) United States Patent
Perrier

(10) Patent No.: US 11,751,992 B2
(45) Date of Patent: Sep. 12, 2023

(54) MECHANICAL PROSTHETIC HEART VALVE

(71) Applicant: Novostia SA, Epalinges (CH)

(72) Inventor: Philippe Perrier, Saint-Nom-la-Bretèche (FR)

(73) Assignee: Novostia SA, Epalinges (CH)

( * ) Notice: Subject to any disclaimer, the term of this patent is extended or adjusted under 35 U.S.C. 154(b) by 52 days.

(21) Appl. No.: 17/146,150

(22) Filed: Jan. 11, 2021

(65) Prior Publication Data
US 2021/0212815 A1    Jul. 15, 2021

(30) Foreign Application Priority Data
Jan. 14, 2020  (CH) ................................ CH00045/20

(51) Int. Cl.
*A61F 2/24*    (2006.01)
(52) U.S. Cl.
CPC .......... *A61F 2/2403* (2013.01); *A61F 2/2418* (2013.01); *A61F 2230/0023* (2013.01)
(58) Field of Classification Search
CPC .................. A61F 2/2403; A61F 2/2418; A61F 2230/0023
See application file for complete search history.

(56) References Cited

U.S. PATENT DOCUMENTS

| 4,363,142 | A | 12/1982 | Meyer |
| 4,820,299 | A | 4/1989 | Philippe et al. |
| 5,123,918 | A | 6/1992 | Perrier et al. |

(Continued)

FOREIGN PATENT DOCUMENTS

| AU | 2003244523 A1 | 9/2003 |
| AU | 2013200056 A1 | 1/2013 |

(Continued)

OTHER PUBLICATIONS

International Search Report & Written Opinion for PCT/IB2021/050148, dated Mar. 9, 2021, 5 pgs.

(Continued)

*Primary Examiner* — Paul B Prebilic
(74) *Attorney, Agent, or Firm* — Blank Rome LLP

(57) ABSTRACT

The invention relates to a mechanical prosthetic heart valve (10) comprising an annular support (12) having an internal peripheral wall (14) centered about a longitudinal axis (X) and delimiting an internal passage, and at least two mobile leaflets (40), preferably three leaflets (40), arranged in such a way as to each be able to effect a rotational movement about an axis of rotation perpendicular to said longitudinal axis (X) so that the valve (10) can pass from a closed configuration to an open configuration and vice versa. Each leaflet comprises a central part (46), and two lateral winglets (48a, 48b) flanking the central part (46) symmetrically with respect to a plane of symmetry (Z) of the leaflet. Each winglet (48a, 48b) comprises one of two terminal portions (49a, 49b). The annular support (12) comprising two opposite edges (26, 28) and as many extensions (30) as the number of leaflets, which extend axially from one of the opposite edges (26, 28), a profiled recess (32) being created on two opposite sides of each extension (30), the recesses (32) acting as guide surfaces for the respective terminal portions (48a, 48b) of each leaflet (40) as the valve (10) passes from an open configuration to a closed configuration, and vice versa. A contact zone of each leaflet (40) in the open position with the internal peripheral wall (14) is less than 15% of the total width of the leaflet (40) extending between the extremities of the two terminal portions (49a, 49b).

18 Claims, 11 Drawing Sheets

(56) References Cited

U.S. PATENT DOCUMENTS

| | | | |
|---|---|---|---|
| 5,197,980 A | 3/1993 | Gorshkov | |
| 5,207,707 A | 5/1993 | Gourley | |
| 5,314,467 A * | 5/1994 | Shu | A61F 2/2403 |
| | | | 137/527 |
| 5,843,183 A | 12/1998 | Bokros et al. | |
| 6,068,657 A | 5/2000 | Lapeyre et al. | |
| 6,183,510 B1 | 2/2001 | Otto et al. | |
| 6,395,024 B1 * | 5/2002 | Lapeyre | A61F 2/2403 |
| | | | 623/2.22 |
| 9,775,708 B2 | 10/2017 | Sievers | |
| 10,182,907 B2 | 1/2019 | Lapeyre | |
| 2008/0086202 A1 | 4/2008 | Lapeyre | |
| 2010/0131056 A1 * | 5/2010 | Lapeyre | A61F 2/2403 |
| | | | 623/2.27 |
| 2021/0212814 A1 | 7/2021 | Perrier | |
| 2021/0212815 A1 | 7/2021 | Perrier | |

FOREIGN PATENT DOCUMENTS

| | | |
|---|---|---|
| CN | 103099688 A | 5/2013 |
| DE | 102012216742 A1 | 3/2014 |
| EP | 0289404 A2 | 11/1988 |
| EP | 0338179 A1 | 10/1989 |
| EP | 0383676 A1 | 8/1990 |
| EP | 0963739 A1 | 12/1999 |
| EP | 1083845 A1 | 3/2001 |
| FR | 2915678 A1 | 11/2008 |
| WO | WO-99/62437 A1 | 12/1999 |
| WO | WO-2008/152224 A2 | 12/2008 |
| WO | WO-2016/137321 A1 | 9/2016 |

OTHER PUBLICATIONS

International Search Report & Written Opinion for PCT/IB2021/050149, dated Mar. 16, 2021, 5 pgs.
International Search Report & Written Opinion for PCT/B2021/050150, dated Mar. 22, 2021, 5 pgs.
Switzerland Search Report for CH Application No. CH 452020, dated May 4, 2020, 2 pgs.
M. S. Zakaria, et al.. "Review of Numerical Methods for Simulation of Mechanical Heart Valves and the Potential for Blood Clotting", Med Biol Eng Comput, 2017, vol. 55, pp. 1519-1548.

* cited by examiner

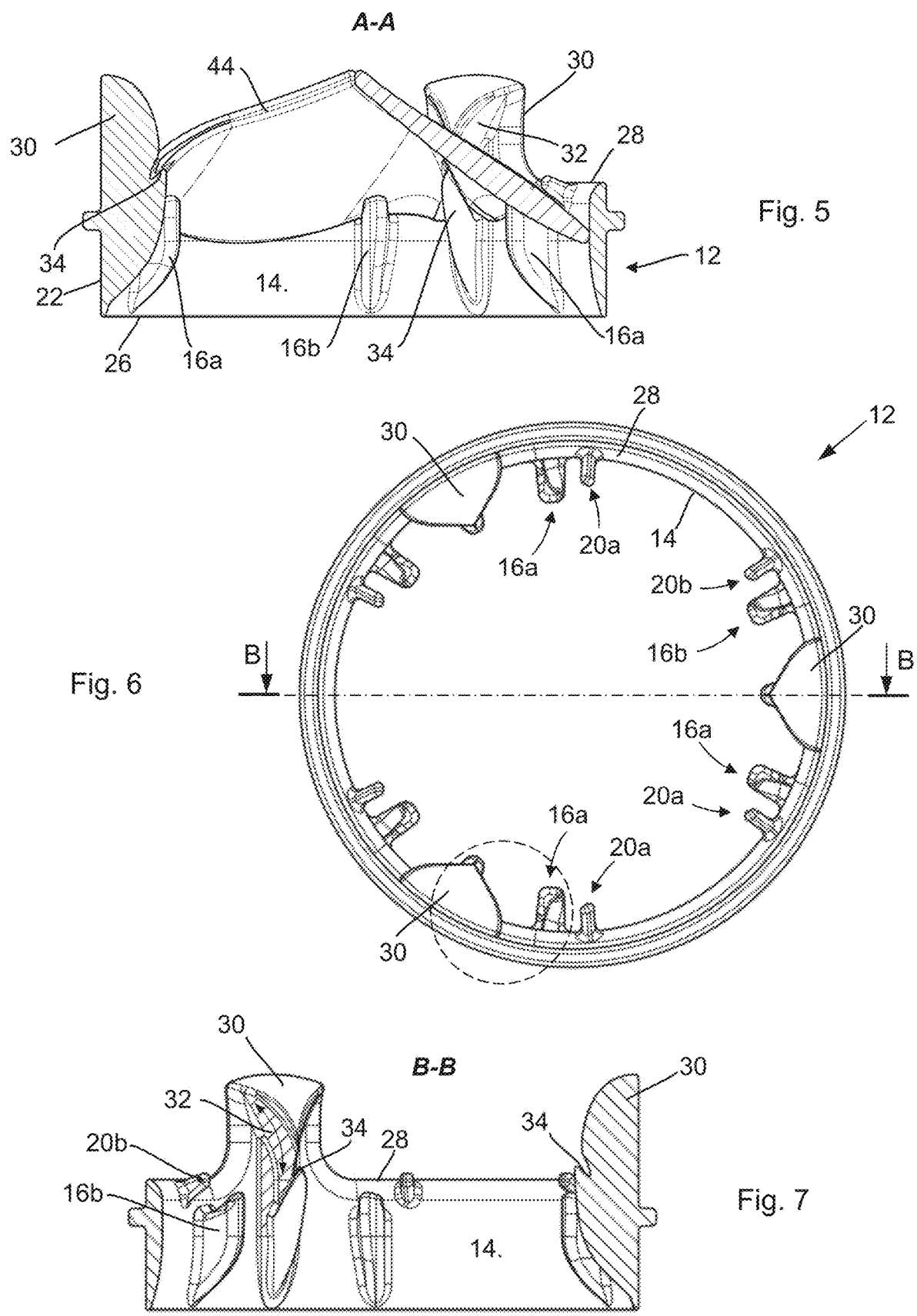

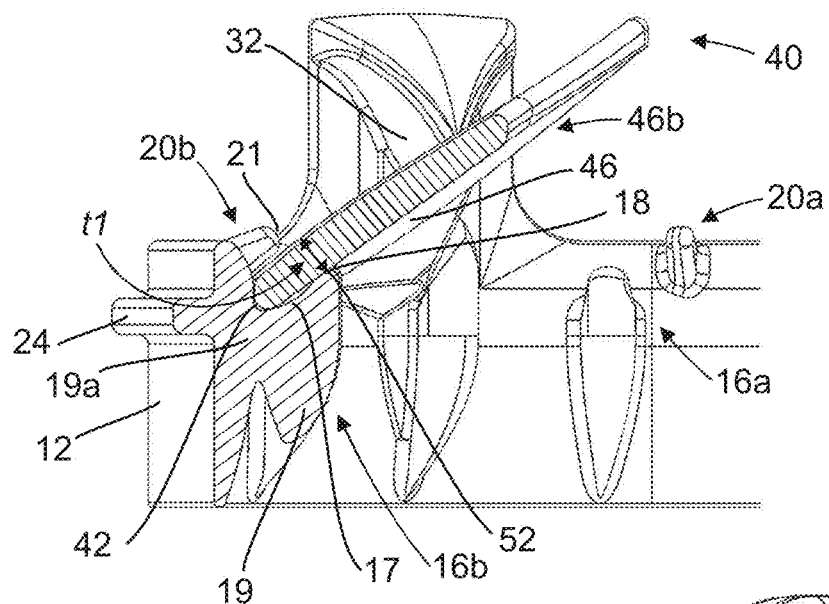
Fig. 13
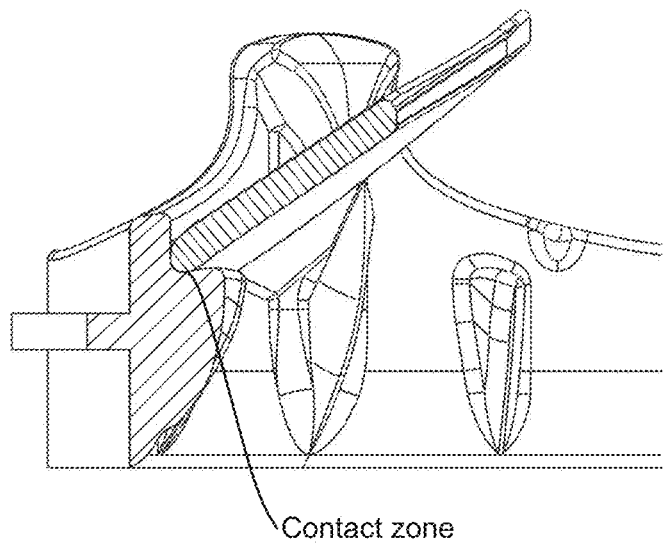
Fig. 14 – prior art
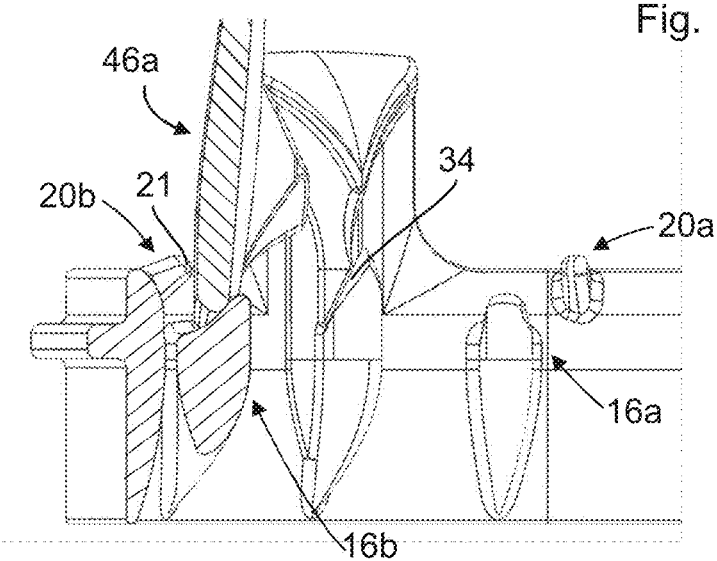
Fig. 15

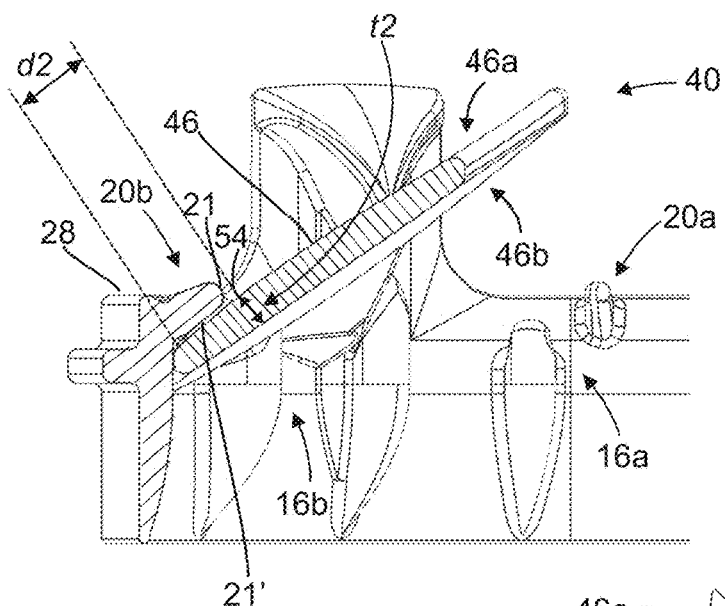
Fig. 16
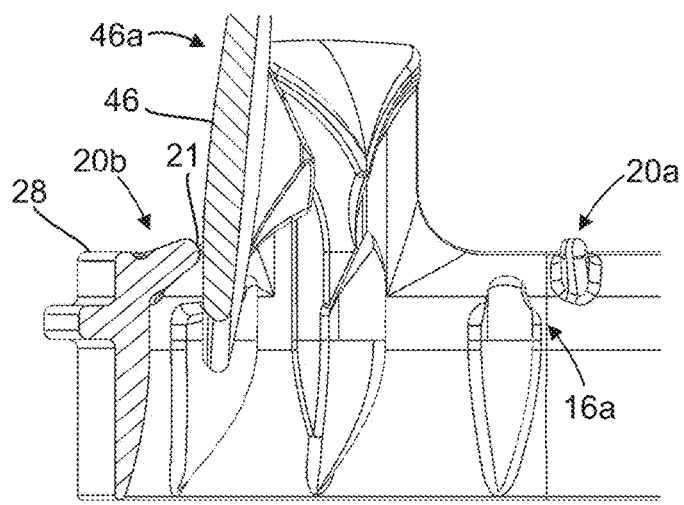
Fig. 17
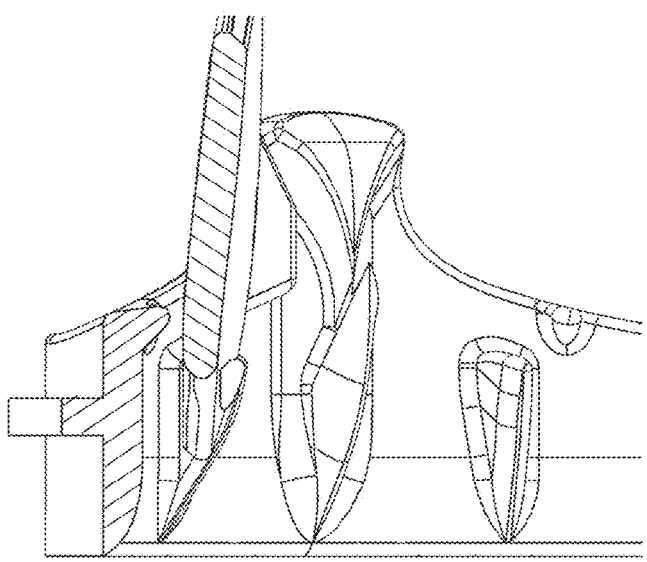
Fig. 18 – prior art

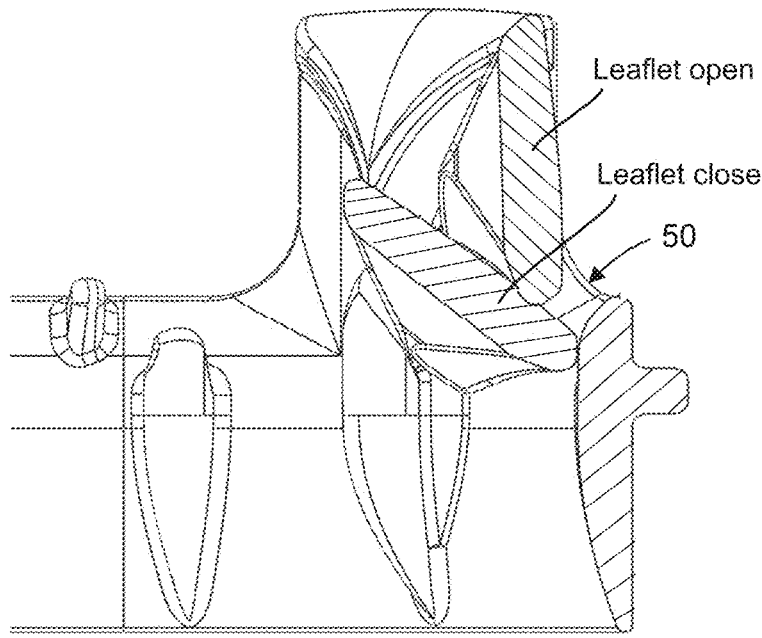
Fig. 19
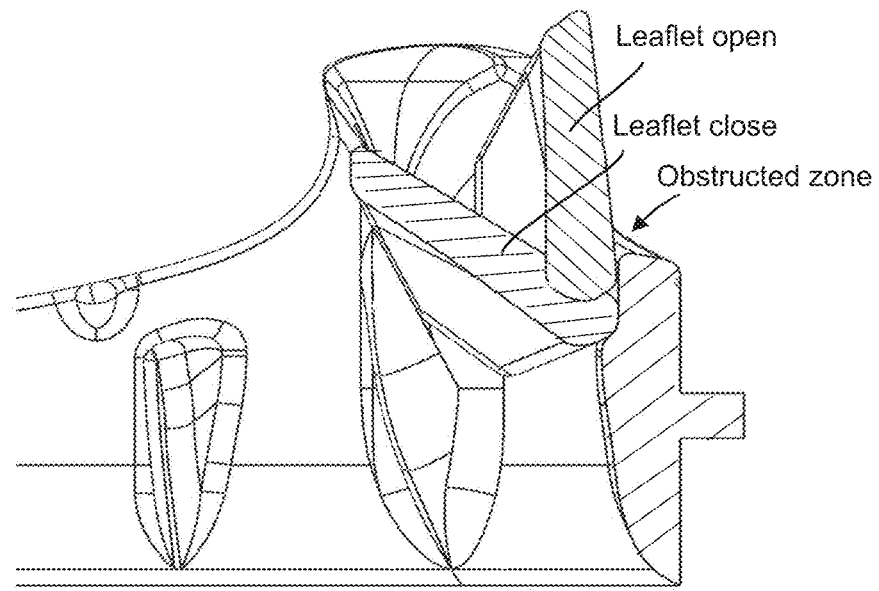
Fig. 20 – prior art

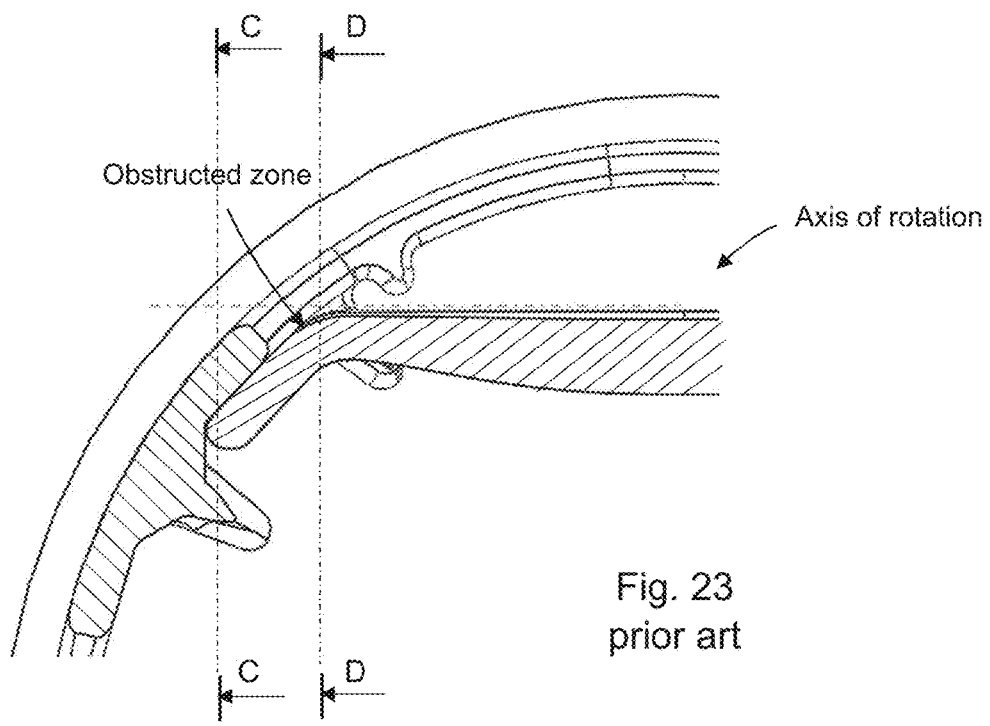
Fig. 23
prior art
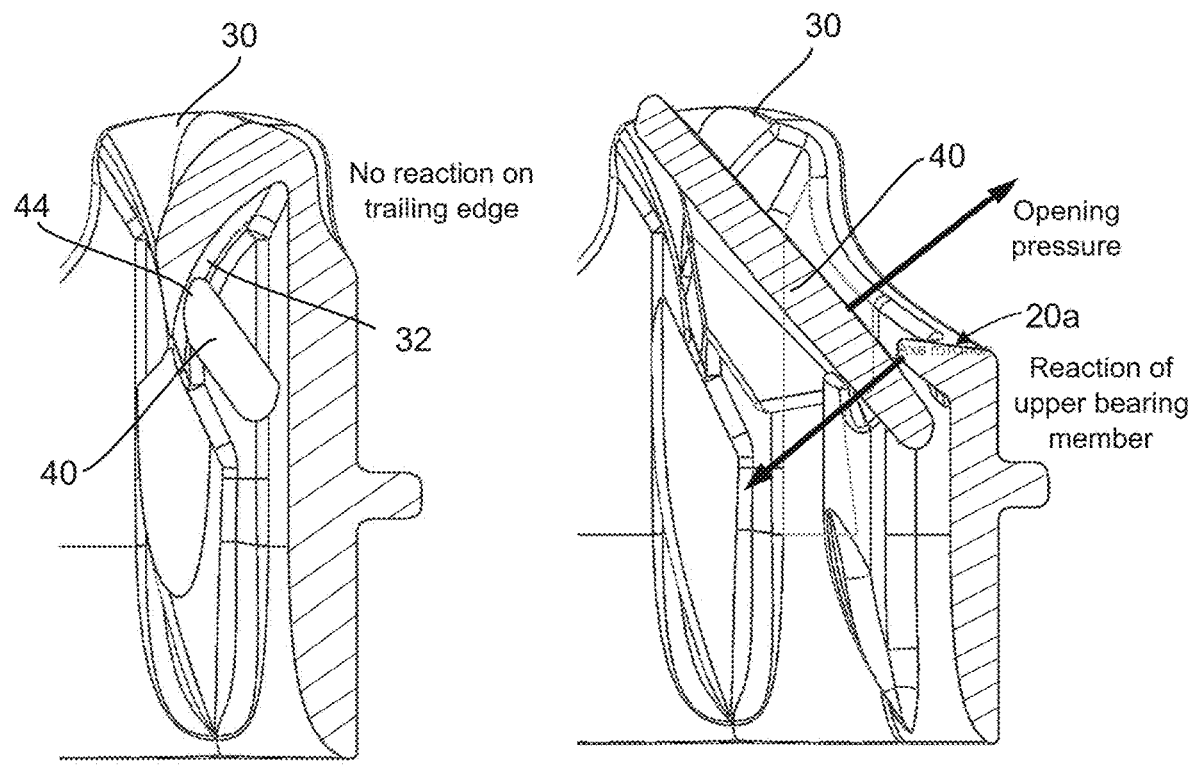
A-A
Fig. 24
B-B
Fig. 25

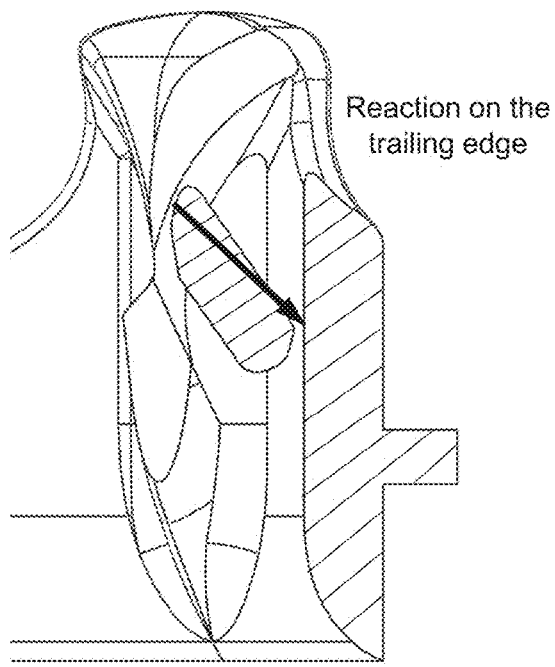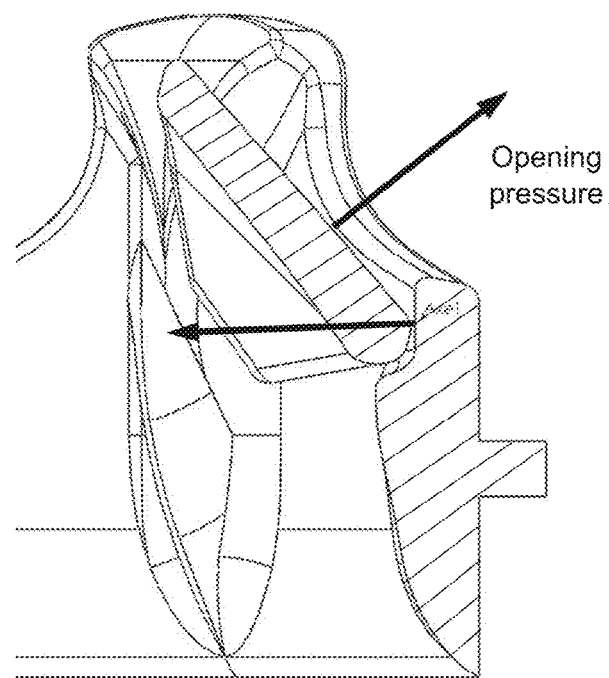
Fig. 26 – prior art  Fig. 27 – prior art

MECHANICAL PROSTHETIC HEART VALVE

RELATED APPLICATION

The present application claims priority to Swiss Application No. CH 00045/20, filed Jan. 14, 2020, the entire contents of which are hereby incorporated by reference.

TECHNICAL FIELD

The present invention relates to a mechanical prosthetic heart valve.

PRIOR ART

A distinction is made between two broad families of prosthetic heart valves. One of these families covers valve prostheses made of flexible tissue arranged on rigid struts in order to mimic the natural valves, referred to as tissue valves. The other of these families covers mechanical valve prostheses which are devices with no relationship to the shape of a natural valve and which are manufactured from wear-resistant and biologically compatible artificial materials.

Because of their anatomical configuration and physiological mode of operation, tissue valves offer biological performance aspects similar to those of a natural heart valve because they conform to the natural structure of the flow of blood through the chambers of the heart and through the aorta.

This particular feature of tissue valves allows patients to save on the need for an anticoagulant treatment for the rest of their lives, and this eliminates the risk of hemorrhagic accidents as a consequence of the long-term administration of these medicaments and therefore affords these patients a better quality of life. In this way, the patient may forget that he has a heart valve fitted.

However, these tissue valves have a limited life because they unavoidably become calcified over time, which means that they need to be replaced after ten years or so on average. Because of their limited life, this type of prosthesis is, in most cases, intended for subjects over 65 years of age or subjects whose life expectancy is shorter than the life of the tissue valves.

Unlike tissue valves, artificial valve devices of mechanical type do not degrade and have a life that exceeds the span of human life. Since the start of the 1960s, several generations of mechanical heart valves have been successively designed. Mention may be made, for example, of the valve prostheses consisting of a caged ball (STARR-EDWARDS), then, at the start of the 1970s, the second-generation prostheses consisting of a tiling disk (BJORK-SHILEY) and then, ten years later, the side-opening bi-leaflet third-generation prostheses of the ST-JUDE MEDICAL type.

EP1083845 discloses a mechanical prosthetic heart valve comprising an annular support and three leaflets, each one comprising two winglets collaborating with the annular support to allow the heart valve to pass from an open position to a closed position and vice versa. The annular support comprises three pairs of lateral openings referred to as windows. Each pair of windows is arranged in correspondence with the winglets of the associated leaflet. The windows allow the blood to flow to the rear of the winglets of each leaflet and flush a large proportion of the pivot region of the leaflet in the open and closed position. This flushing ought to help reduce the stagnation of blood behind the winglets, and thus reduce the probability of the formation of a local blood clot or a thrombus in this region. However, in-vivo testing in calves in this specific configuration has demonstrated that the downstream strut of the window, on which the leaflet rests in the open position, in fact constitutes an obstacle placed in the flow during systole. This obstacle is liable to promote the formation of thrombus.

WO2008152224 discloses a mechanical prosthetic heart valve of the latest generation. This heart valve comprises an annular support comprising an internal peripheral surface centered around a longitudinal axis and delimiting an internal passage as well as three leaflets arranged in such a way as to each be able to effect a rotational movement about an axis of rotation perpendicular to the longitudinal axis so that the valve can pass from a closed configuration to an open configuration and vice versa. The leaflets between them delimit a main orifice centered on the longitudinal axis and through which the blood can flow axially when the valve is in the open configuration, whereas these leaflets obstruct the internal passage of the annular support so as to be able to prevent the blood from flowing back through the main orifice when the valve is in the closed configuration. Each leaflet comprises a leading edge designed to come against a portion of the internal peripheral surface of the annular support when the valve is in the closed configuration, a central part comprising an exterior surface and an interior surface, and two lateral winglets flanking the central part symmetrically and which are inclined with respect to this central part.

According to the configuration of the valve described in this document, the leading edges of the two winglets of each leaflet remain very close to or in contact with the internal peripheral surface of the annular support as the leaflets rotate into all the positions. Now, this may lead to the creation of a zone of recirculation of the flow downstream of the winglets that is liable to encourage platelet aggregation. It could therefore be necessary for the patient to have to take anticoagulants in order to avoid any risk of thrombosis. Adherence to a treatment for life is, however, not straightforward, particularly in the case of young people, and particularly young woman of childbearing age.

Furthermore, the friction at the leading edges of the two winglets of each leaflet may present problems of wearing on the leaflets, and this may have a not-insignificant impact on the life of the valve.

It is an object of the present invention therefore to propose a mechanical prosthetic heart valve that minimizes platelet aggregation zones in order to avoid the need to take anticoagulants.

BRIEF SUMMARY OF THE INVENTION

According to the invention, this object is achieved by means of a mechanical prosthetic heart valve comprising an annular support having an internal peripheral wall centered about a longitudinal axis and delimiting an internal passage, and at least two mobile leaflets, preferably three leaflets, arranged in such a way as to each be able to effect a rotational movement about an axis of rotation perpendicular to said longitudinal axis so that the valve can pass from a closed configuration to an open configuration and vice versa. The leaflets between them delimit a main orifice centered on the longitudinal axis and through which the blood can flow axially when the valve is in the open configuration. The leaflets at least partially obstruct the internal passage of the annular support so as to be able to prevent the blood from flowing back through the main orifice when the valve is in the closed configuration. Each leaflet comprises a leading edge designed to come against a portion of the internal peripheral wall of the annular support when the valve is in the closed configuration, an internal surface extending from the leading edge, an external surface opposite the internal surface and extending from the leading edge, and two terminal portions. The annular support comprises two opposite edges and as many extensions as the number of leaflets, which extend axially from one of the opposite edges. A profiled recess is created on two opposite sides of each extension. The recesses act as guide surfaces for the respective terminal portions of each leaflet as the valve passes from an open configuration to a closed configuration, and vice versa. The annular support further comprises, on the internal peripheral wall, two lower bearing members per leaflet which are situated between two of said extensions and designed to be in abutment against the corresponding leaflet when the valve is in a closed configuration.

A contact zone of each leaflet in the open position with the internal peripheral wall is less than 15% of the total width of the leaflet extending between the extremities of the two terminal portions.

In an embodiment, the contact zone of each leaflet in the open position with the internal peripheral wall is less than 10% of the total width of the leaflet.

In an embodiment, the contact zone of each leaflet in the open position with the internal peripheral wall is less than 7.5% of the total width of the leaflet.

In an embodiment, the contact zone of each leaflet in the open position with the internal peripheral wall is less than 5% of the total width of the leaflet.

In an embodiment, each leaflet comprises a central part and two lateral winglets flanking the central part symmetrically with respect to a plane of symmetry of the leaflet. Each lateral winglet comprises an external surface, an internal surface and one of the two terminal portions. Two flow channels are located respectively between one lower bearing member and one adjacent extension of the annular support when the heart valve is in the open configuration.

In an embodiment, the two flow channels are delimited notably by the internal peripheral wall of the annular support and the external surface of the respective two lateral winglets.

In an embodiment, the lateral winglets are inclined with respect to the central part of each leaflet. The lateral winglets have a respective first and second curved proximal end portion extending from the central part with a curved external surface and a respective first and second distal end portion contacting respectively one and another extension of the annular support when the heart valve is in the open configuration. The first and second distal end portions extend substantially parallel to the internal peripheral wall and are aligned with respectively the one and another extensions. The curved external surface of each of the first and second proximal portions curves away from the internal peripheral wall outside respectively said one and another extensions in the open configuration.

In an embodiment, the two flow channels form right from the start of pivoting of each leaflet as the heart valve passes from a closed configuration to an open configuration. The dimensions of the two flow channels which are associated with each leaflet increase as the leaflets progressively pivot until such point as the valve is in the open configuration.

In an embodiment, the surface of the internal peripheral wall of the annular support is a continuous surface devoid of windows at the level of the end portions of each leaflet.

In an embodiment, the leading edge and the external surface of each leaflet are distant by at least 0.2 mm from the internal peripheral wall over at least 75% of the distance of the leading edge separating the two terminal portions of each leaflet when the heart valve is in the open configuration.

In an embodiment, the leading edge and the external surface of each leaflet are distant by at least 0.5 mm from the internal peripheral wall over at least 75% of the distance of the leading edge separating the two terminal portions of each leaflet when the heart valve is in the open configuration.

In an embodiment, the leading edge and the external surface of each leaflet are distant by at least 0.5 mm from the internal peripheral wall over at least 90% of the distance of the leading edge separating the two terminal portions of each leaflet when the heart valve is in the open configuration.

In an embodiment, in a plane perpendicular to the longitudinal axis of the valve, the axis of rotation of each leaflet is situated at a distance from the longitudinal axis that is greater than 75% of the radius of the annular support.

In an embodiment, the distance between the axis of rotation of each leaflet and the external surface of the central part of the leaflet is greater than 0.2 mm.

In an embodiment, the external surface of each leaflet in the open position is at a distance from the internal peripherical wall of the annular support at least equal to 5% of the diameter of the annular support at a plane of symmetry of the leaflet.

In an embodiment, the mechanical prosthetic heart valve to any comprises three leaflets pivotally mounted between three extensions. Six flow channels are formed when the valve is in the open configuration. The flow channels are located adjacent to each lateral side of each extension.

Another aspect of the invention relates to a prosthetic heart valve comprising:

an annular support having an internal peripheral wall and defining an internal passage centered on a longitudinal axis;

a leaflet having a central part with a planar external surface, and a first and second winglet having a respective first and second curved proximal end portion extending from the central part with a curved external surface and a respective first and second distal end portion, said leaflet movable between an open configuration that permits blood to flow through the internal passage in a flow direction along the longitudinal axis, and a closed configuration that prevents blood from flowing through the internal passage in the flow direction; and a first extension and a second extension which each extend axially from the internal peripheral wall, wherein in the opened configuration the first distal end portion contacts said first extension, the first curved proximal end portion is curved toward the second extension, the planar external surface extends linearly toward the second extension, the second distal end portion contacts said second extension and the second curved proximal end portion is curved toward the first extension.

In an embodiment, in the opened configuration, the first distal end portion extends substantially parallel to the internal peripheral wall and is aligned with the first extension and the curved external surface curves away from the internal peripheral wall outside the first extension.

In an embodiment, the prosthetic heart valve further comprises a second and third leaflets and a third extension. In the opened configuration the three leaflets generally form a triangular shape with the distal ends of said leaflets contacting the first, second and third extensions, and the planar external surface of the central parts extending linearly between the first, second and third extension.

BRIEF DESCRIPTION OF THE FIGURES

Examples of implementations of the invention are indicated in the description, which is illustrated by the attached Figures, in which:

FIG. 5 illustrates a view of FIG. 4 in section on A-A;

FIG. 6 illustrates a view of the annular support, from above;

FIG. 7 illustrates a view of FIG. 6 in section on B-B;

FIG. 13 illustrates a partial perspective view of the mechanical prosthetic heart valve in the closed configuration with a partial section in the region of a lower bearing member associated with a leaflet;

FIG. 14 illustrates a view similar to FIG. 13 for a mechanical prosthetic heart valve according to the prior art;

FIG. 15 illustrates a view similar to FIG. 13 when the mechanical prosthetic heart valve is in the open configuration;

FIG. 16 illustrates a partial perspective view of the mechanical prosthetic heart valve in the closed configuration with a partial section in the region of an upper bearing members associated with a leaflet;

FIG. 17 illustrates a view similar to FIG. 16 when the mechanical prosthetic heart valve is in the open configuration;

FIG. 18 illustrates a view similar to FIG. 17 for a mechanical prosthetic heart valve according to the prior art;

FIG. 19 illustrates a partial perspective view of the mechanical prosthetic heart valve with a leaflet in both a closed configuration and an open configuration;

FIG. 20 illustrates a view similar to FIG. 19 for a mechanical prosthetic heart valve according to the prior art;

FIG. 23 illustrates a view similar to FIG. 22 for a mechanical prosthetic heart valve according to the prior art.

FIGS. 24 and 25 are views respectively in section on A-A and on B-B of FIG. 22 to illustrate the forces exerted on the leaflets upon the opening of the valve, and FIGS. 26 and 27 are views respectively in section on C-C and on D-D of FIG. 23 to illustrate the forces exerted on the leaflets upon opening for a mechanical prosthetic heart valve according to the prior art.

EXAMPLES OF EMBODIMENT OF THE INVENTION

Figure 1:
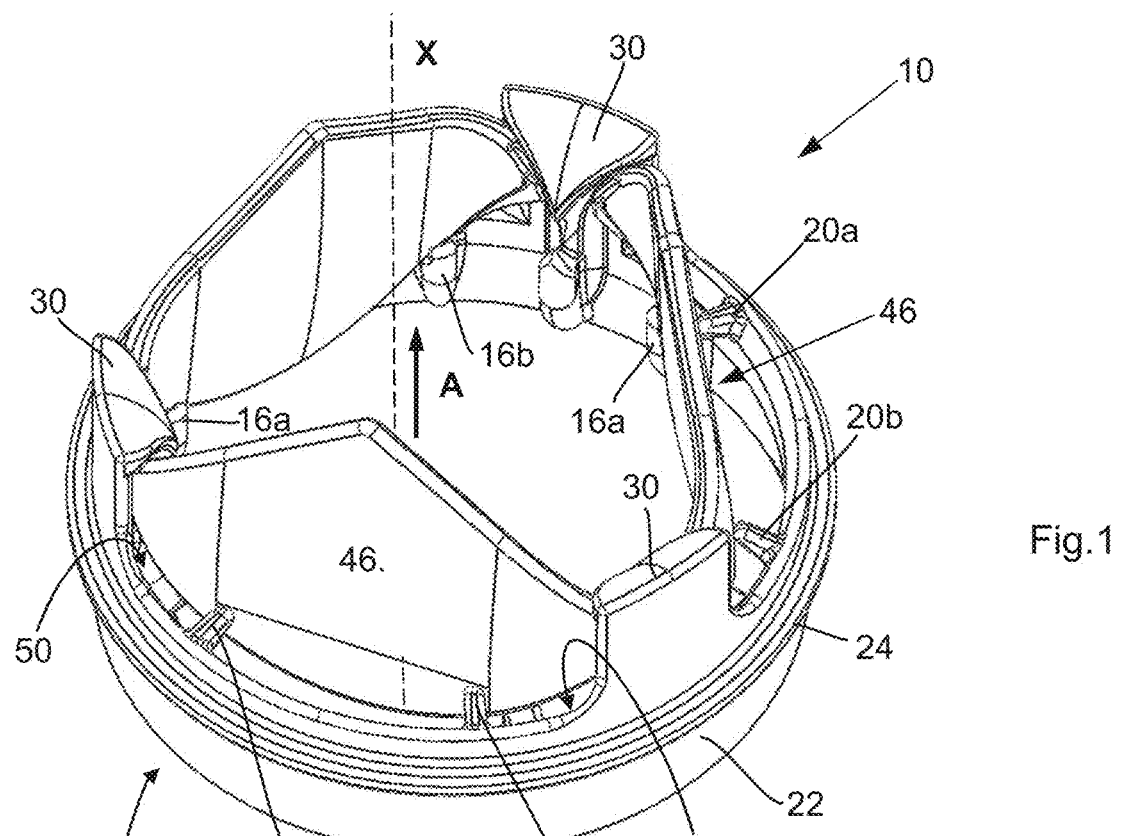
FIG. 1 illustrates a perspective view of the mechanical prosthetic heart valve in an open configuration in which the leaflets between them delimit a main orifice through which the blood can flow.

In describing the illustrative, non-limiting embodiments illustrated in the drawings, specific terminology will be resorted to for the sake of clarity. However, the disclosure is not intended to be limited to the specific terms so selected, and it is to be understood that each specific term includes all technical equivalents that operate in similar manner to accomplish a similar purpose. Several embodiments are described for illustrative purposes, it being understood that the description and claims are not limited to the illustrated embodiments and other embodiments not specifically shown in the drawings may also be within the scope of this disclosure.

As illustrated notably in FIGS. 1 to 4, a mechanical prosthetic heart valve 10 comprises a ring-shaped annular support 12 which within it defines a central internal passage 9 (also see FIG. 6) for the cyclic flow of blood under the action of the contractions of the heart. The flow passing through the heart valve 10 when the latter is in the open position is qualified as an antegrade flow and its direction of flow (also referred to herein as the outflow direction) is indicated by the arrow A in FIG. 1. By opposition, the flow flowing in the opposite direction (also referred to herein as the inflow direction) when the heart valve 10 closes, is qualified as a retrograde flow.

The central internal passage for the flow of blood is delimited by an internal peripheral wall 14 (FIG. 5) of the annular support 12 which acts as a support for three mobile leaflets 40. As depicted in FIG. 1, the annular support 12 of the heart valve 10 is centered around a longitudinal axis X and exhibits symmetry of revolution about this axis. It will be noted that the valve may, without this affecting the principle of the invention, comprise just two leaflets, in which case the annular support 12 is of elliptical shape and the leaflets are oval in shape, or may comprise more than three leaflets.

The annular support 12 also comprises an exterior peripheral wall 22 exhibiting a peripheral rim 24 intended to accept a suture ring, not depicted, for example made of textile, and which allows the surgeon to attach the valve to the heart tissues using sutures in the known way.

Figure 2:
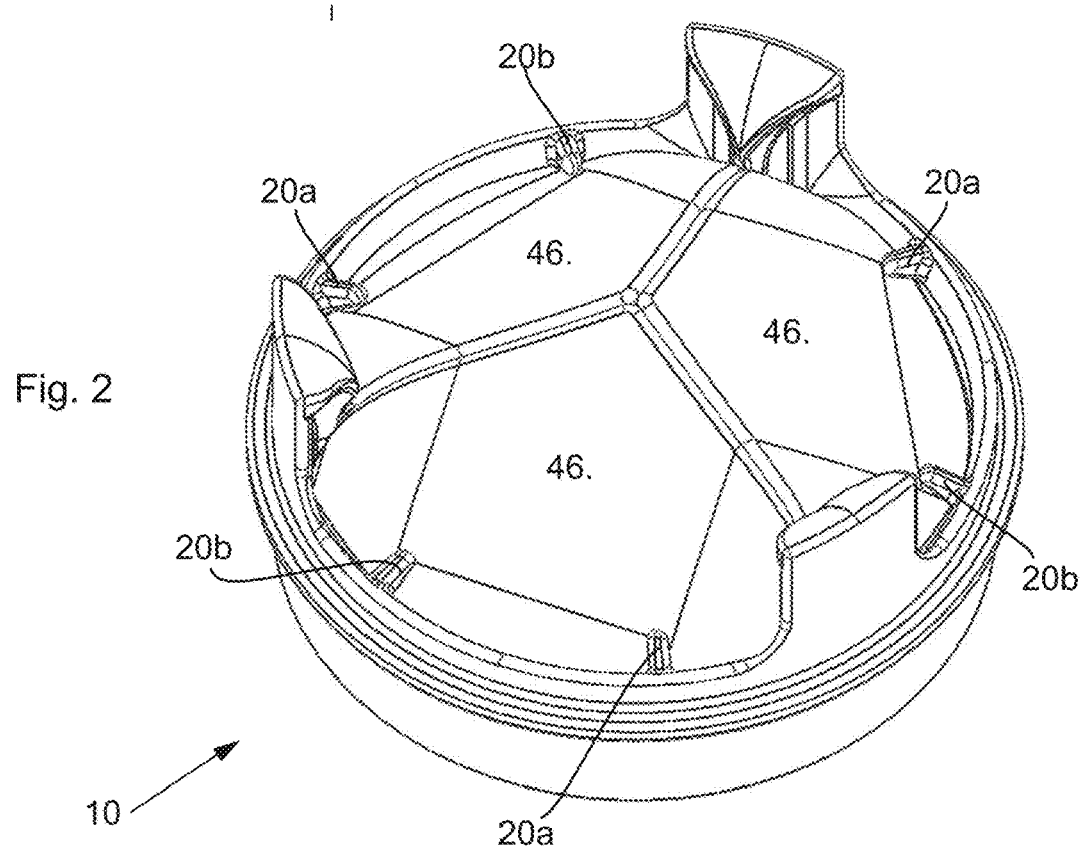
FIG. 2 illustrates a perspective view of the mechanical prosthetic heart valve in a closed configuration in which the leaflets obstruct the internal passage of the annular support so as to be able to prevent the blood from flowing back through the main orifice.
Figure 3:
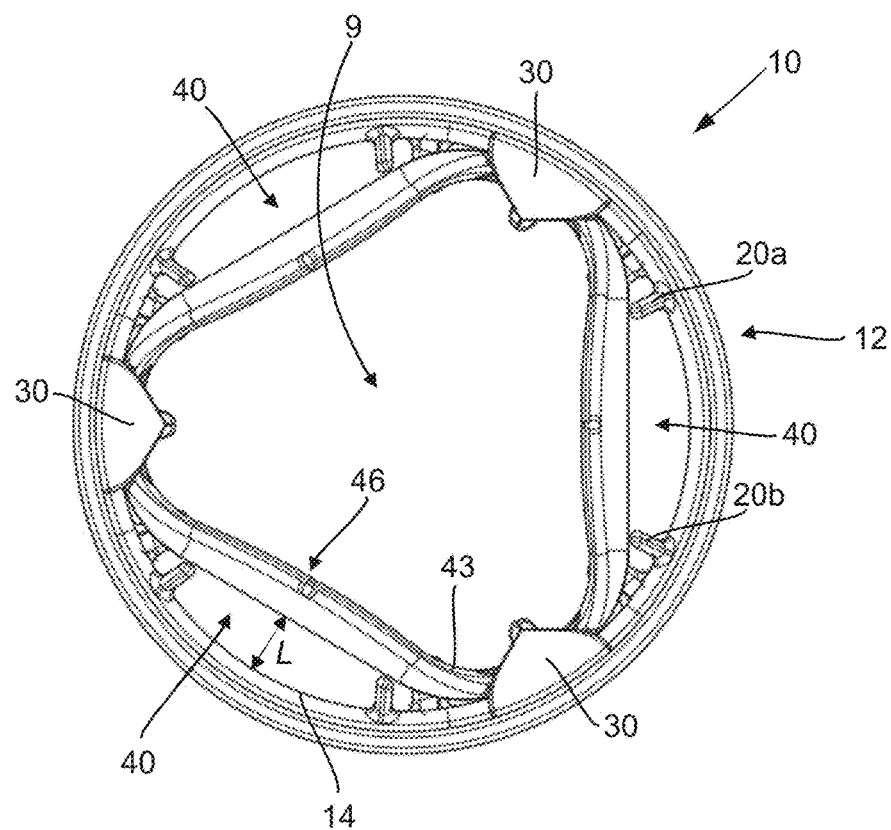
FIG. 3 illustrates a view of FIG. 1, from above.
Figure 4:
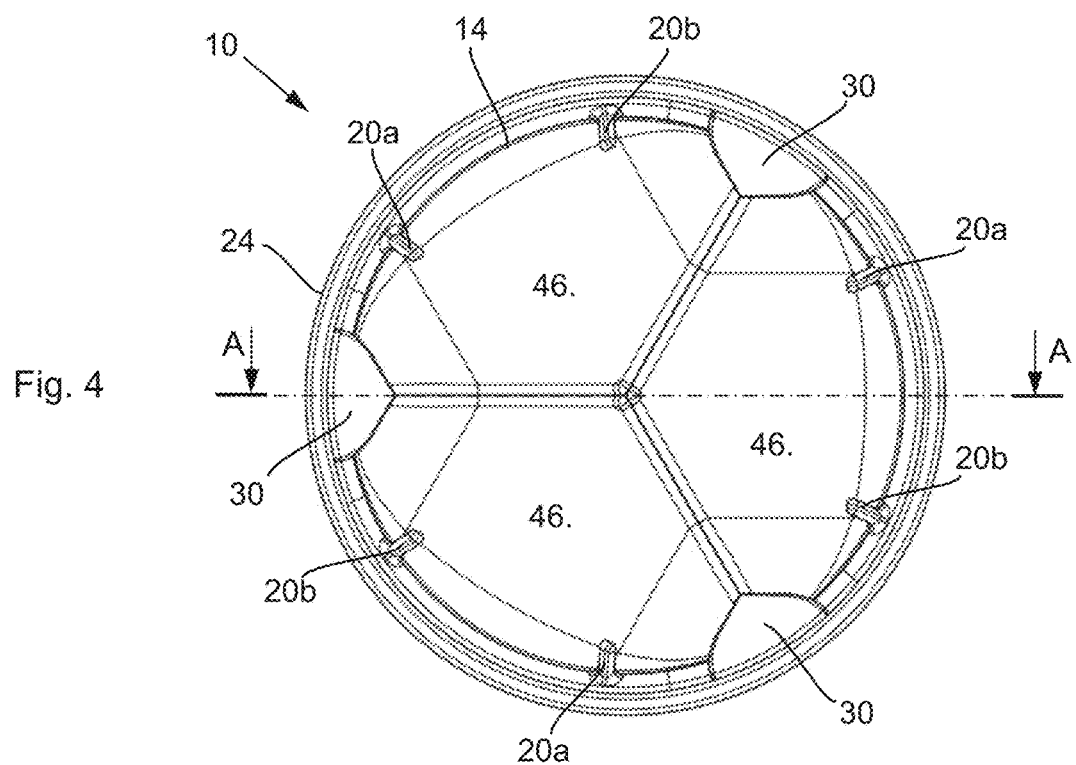
FIG. 4 illustrates a view of FIG. 2, from above.

In FIGS. 1, 3, the heart valve 10 is depicted in the open configuration in which the leaflets 40 are in what is known as the raised or open position, the flow of blood passing through the valve in the outflow direction, whereas in FIGS. 2, 4, the valve is depicted in the closed configuration with the leaflets in what is referred to as the lowered or closed position, preventing blood flow through the heart valve 10 in the inflow direction.

As can be seen in FIG. 5, the annular support 12 comprises an upstream edge or leading edge 26 connecting the internal peripheral wall 14 to the exterior peripheral wall 22 and which is positioned on the upstream side of the antegrade flow. The annular support 12 also comprises a downstream edge or trailing edge 28 which is positioned on the downstream side of the antegrade flow and which likewise connects the internal peripheral wall 14 to the exterior peripheral wall 22 of the annular support.

With particular reference to FIGS. 6 and 7, the support 12 also comprises three guiding extensions 30 which extend from the trailing edge 28 in the outflow direction, parallel to the direction of the longitudinal axis X. The guiding extensions 30 thus form projections or crenellations extending axially with respect to the trailing edge 28 and the base of which is substantially the same width (dimension perpendicular to the axis X) as the tip. These guiding extensions 30 house profiled recesses 32, in the form of surfaces of revolution, with which terminal portions of the mobile leaflets, which will be described later, collaborate so that the heart valve 10 can pass from a closed configuration to an open configuration and vice versa.

Figure 11:
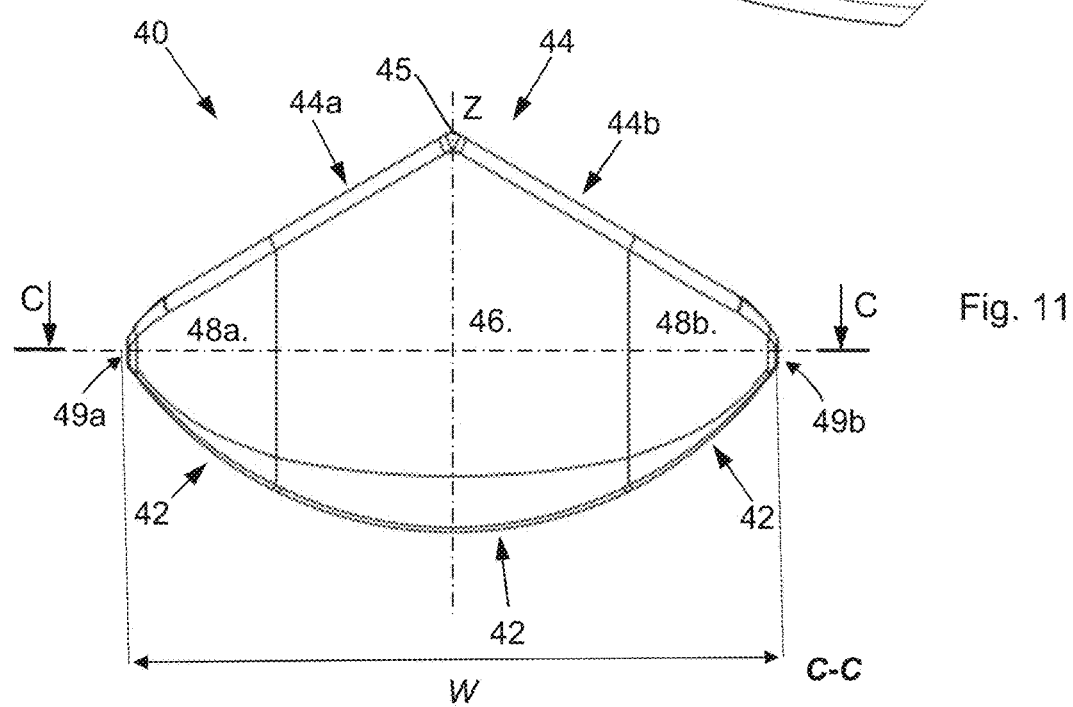
FIG. 11 illustrates a view of a leaflet from above, from the side of its external surface.

With reference notably to FIG. 11, each leaflet 40 is identical to all the other leaflets with which the heart valve 10 is equipped. The leaflet 40 comprises a central part 46 to which there are connected two lateral winglets 48a, 48b flanking this central part symmetrically and which are inclined with respect thereto as can be seen in particular in FIG. 12. The central part 46 has an external surface 46a and an internal surface 46b, each of which are substantially planar though in one embodiment the internal surface 46b and/or the external surface 46a can be slightly curved (as shown for the inwardly curved internal surface 46b in FIG. 12) to optimize flow characteristics.

The winglets 48a, 48b have an external surface 47a and an internal surface 47b, as well as a proximal end portion 43a, 43b and a distal end portion 41a, 41b, respectively. The external surface 47a of the distal end portions 41a, 41b can be substantially planar or slightly curved. The proximal end portion 43a, 43b is contiguous with the central part 46 and forms a gentle curve inward to the internal passage 9 so that the distal end portion 41a, 41b forms an angle with respect to the central part 46. In particular, the external surface 47a of the distal end portions 41a, 41b of the winglets 48a, 48b form an angle with respect to the external surface 46a of the central part 46, which in one embodiment can be between 45 and 60 degrees. The leaflet 40 is symmetrical with respect to a plane of symmetry Z. The leaflets 40 are rigid, and can be formed of a rigid material, such as PEEK.

Referring to FIG. 11, the leaflet 40 comprises a trailing point 45, two terminal portions 49a, 49b, a first trailing edge 44a that extends between the trailing point 45 and the first terminal portion 49a, a second trailing edge 44b that extends between the trailing point 45 and the second terminal portion 49b, and a curved leading edge 42 that extends between the first terminal portion 49a and the second terminal portion 49b within the width W of the leaflet 40. Those elements together generally define a triangular shape with an elongated curved leading edge 42. The external and internal surfaces 46a, 46b of the central part 46 and winglets 48a, 48b is positioned between, and does not include, the trailing point 45 and the terminal portions 49a, 49b. It is noted that the leading edge 42 (as well as the trailing edges 44) can be rounded, and the external and internal surfaces 46a, 46b are defined to extend from those rounded edges.

When the leaflet is in the open position, as depicted in FIGS. 1 and 3, the leading edge 42 is positioned on the upstream side of the antegrade flow and, in the closed position, mates with the internal wall 14 of the annular support 12 to form a seal that prevents blood flow from passing, as can be seen in FIG. 4. The leading edge 42 of the leaflet extends from a first terminal portion 49a to a second terminal portion 49b these being situated at the distal ends of the respective lateral winglets 48a, 48b. The leading edge 42 is curved to match the curvature of the internal wall 14.

Furthermore, the leaflet 40 comprises, on the opposite side of the leaflet to the side on which the leading edge 42 is situated, a trailing edge 44 which is positioned on the downstream side of the antegrade flow. The trailing edge 44 comprises two symmetrical portions 44a, 44b which extend respectively from the lateral winglets 48a, 48b as far as a downstream end zone where they meet to form a point 45. The point 45 is aligned with the plane of symmetry Z of the leaflet.

The heart valve 10 also comprises several lower (i.e., on the upstream or leading side) bearing or support members which are different for each leaflet (each leaflet has its own bearing members 16a, 16b) and which are created on the internal peripheral wall 14 of the annular support 12. In particular, with reference notably to FIG. 6, two lower support or support members 16a, 16b (also referring to here as lower bearing or lower bearing members) are arranged between two neighboring guiding extensions 30 to support each leaflet 40 when the heart valve 10 is in a closed configuration. The lower bearing members 16a, 16b are positioned on the upstream side of the leaflets 40 facing the internal surface 46b of the leaflets 40.

Figure 8:
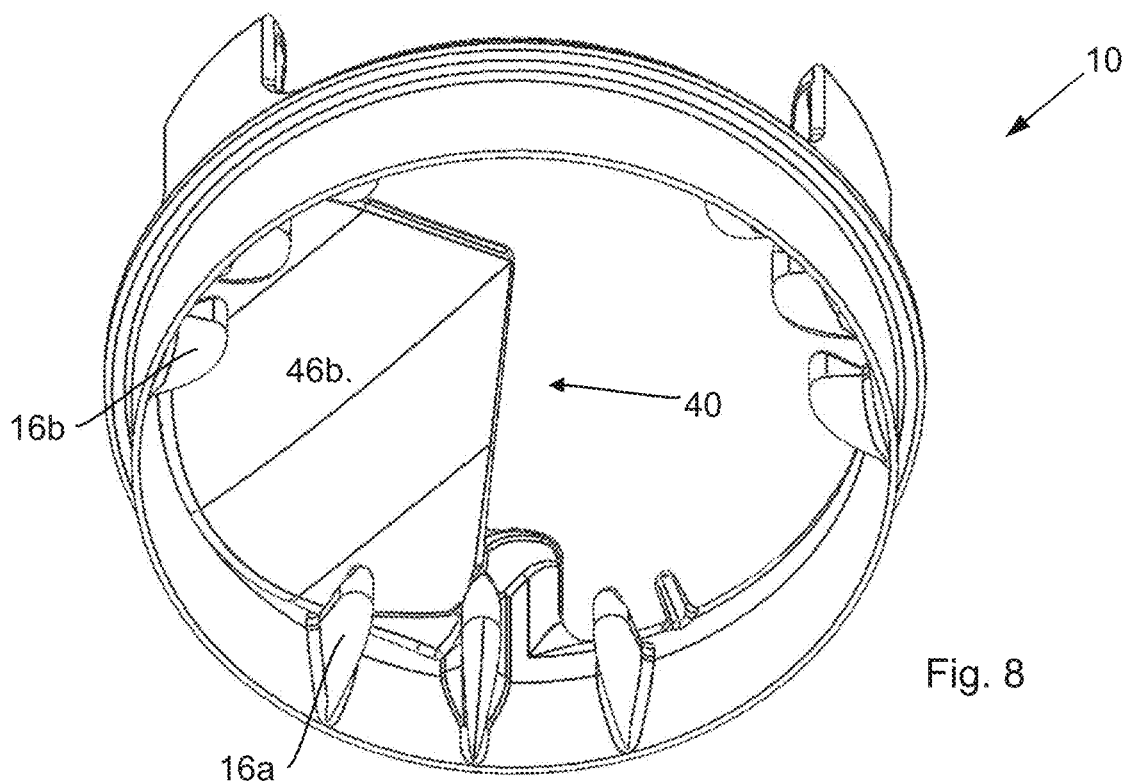
FIG. 8 illustrates a perspective view of the underside of the valve with only one leaflet.

According to FIG. 13, the two lower bearing members 16a, 16b associated with each leaflet comprise each a support body 19 with a proximal end 19a, an intermediate portion, and a distal end forming an apex 18. The intermediate portion has a trailing edge that defines a curved guiding surface 17. The proximal end 19a is at a proximal side of the lower bearing members 16a, 16b at the juncture between the support body 19 and the inner surface 14, and has a curve with a radii of curvature. The apex 18 extends further in the outflow direction than the leading edge 42 and is situated at a distal end of the guiding surface 17, as may also be seen in FIGS. 8 and 13. The intermediate portion of the guiding surface 17 is located between the proximal end 19a and the apex 18 and is curved away from the apex 18 in the inflow direction upstream to the antegrade flow.

In addition, the lower bearing members 16a, 16b are aligned with the central part 46 of the leaflet 40. Thus, in the closed position, a lower bearing zone 52 is formed where the central part 46 of the internal surface 46b of the leaflet 40 comes into contact with the apex 18 of the guiding surface 17. The lower bearing zone 52 includes an apex bearing zone (i.e., the part of the apex 18 that touches the leaflet) and the leaflet bearing zone (i.e., the part of the leaflet internal surface 46b that touches the apex 18). The apex bearing zone and the leaflet bearing zone cooperate to stop the leaflet 40 as it moves from the opened position to the closed position in the antegrade outflow direction; which in turn defines the closed position for the leaflet 40. However, since the intermediate portion is curved away from the leaflet 40, there may be a gap between the intermediate portion of the guiding surface 17 and the leaflet 40, as illustrated in FIG. 13. That is, in the embodiment of FIG. 13, the guiding surface 17 extends inward into the central passage, and upward (i.e., in the outflow flow direction) to the apex 18.

Moreover, the apex 18 does not touch the leading edge 42, but instead contacts a portion of the internal surface 46b set back from the leading edge 42. Thus, the apex 18 is positioned sufficiently far from the leading edge 42 to avoid wear of the leading edge 42 and for the apex 18 to provide structural support, but not too far to interrupt flow. It is further noted that in one embodiment the apex 18 of the lower bearing members 16a, 16b has a width. Accordingly, the apex and leaflet bearing zones are not a finite point, but can be linear or the apex 18 can be a flat surface (e.g., rectangular or square) to further support the leaflet internal surface 46b and distribute the force of the leaflet 40 contacting the apex 18 and further reduce any hammering effect.

The leading edge 42 of each leaflet slides, at least in part, along the guiding surfaces 17 of the two lower bearing members 16a, 16b as the valve passes from an open configuration to a closed configuration. The leading edge 42 and the internal surface 46b of the central part 46 of each leaflet 40 are in contact with the two lower bearing members 16a, 16b illustrated notably in FIG. 6 when the valve 10 is in a closed configuration as can be seen particularly in FIGS. 8 and 9.

The configuration of the lower bearing members 16a, 16b has the advantage of significantly reducing the wearing of the leaflets by spreading the contact zones, unlike the heart valve according to WO2008152224 in which the contact zones are concentrated at the leading edge of the leaflet as illustrated in FIG. 14, something which may lead to premature wearing of the leaflets in this zone, thus reducing the optimal service life of the heart valve. This configuration in particular ensures that the bearing of the leaflet in the closed configuration occurs over its internal surface 46b. Since the internal surface 46b is substantially flat, it has large radii of curvature (see FIGS. 8 and 9). Thus, the internal surface 46b need not be completely flat, but have a sufficiently large radii to increase the contact surface. The radii of the internal surface 46a are at least larger than the thickness of the leaflet, which is larger than the radii at the leading edge. Only the apex 18 of the guiding surface 17 contacts the internal surface 46b of the central part 46 in the closed position. Importantly, the leading edge 42 of the leaflet 40 does not contact the apex 18 and is not utilized to stop movement of the leaflet; which therefore avoids wearing of the leading edge 42, avoids any hammering effect on the leading edge 42, and ensures a reliable seal between the leading edge 42 and the internal wall 14 in the closed position. The very low risk of wearing has the advantage of increasing the diversity of materials that can be employed.

The applicant has found that with respect to the present heart valve 10, the wearing on the leaflet 40 at the zones of contact of the lower bearing members 16a, 16b can be up to 30 microns during accelerated wearing tests; whereas under the same conditions the wearing on the zones of contact of the support members disclosed in WO2008152224 was in excess of 100 microns, which can result in leaflet 42 coming free from the valve 10.

Thus, it is one aspect of the disclosure that the leading edge 42 of the leaflet not be utilized to stop the motion of the leaflet when the leaflet moves into the closed position. In one embodiment, the leading edge 42 (which may include part of a rotational curvature at the leading edge) stays in contact with the guiding surface 17 during rotation of the leaflet from the opened position to the closed position, and the internal surface 46b only comes into contact with the apex 18 in the closed position. In that case, the lower bearing zone 52 is positioned away from the leading edge 42 and also away from any rotational curvature of the leading edge 42, so that the bearing zone 52 does not include any part of the leaflet that is involved in rotation of the leaflet, to avoid added wear on the rotational elements.

Figure 9:
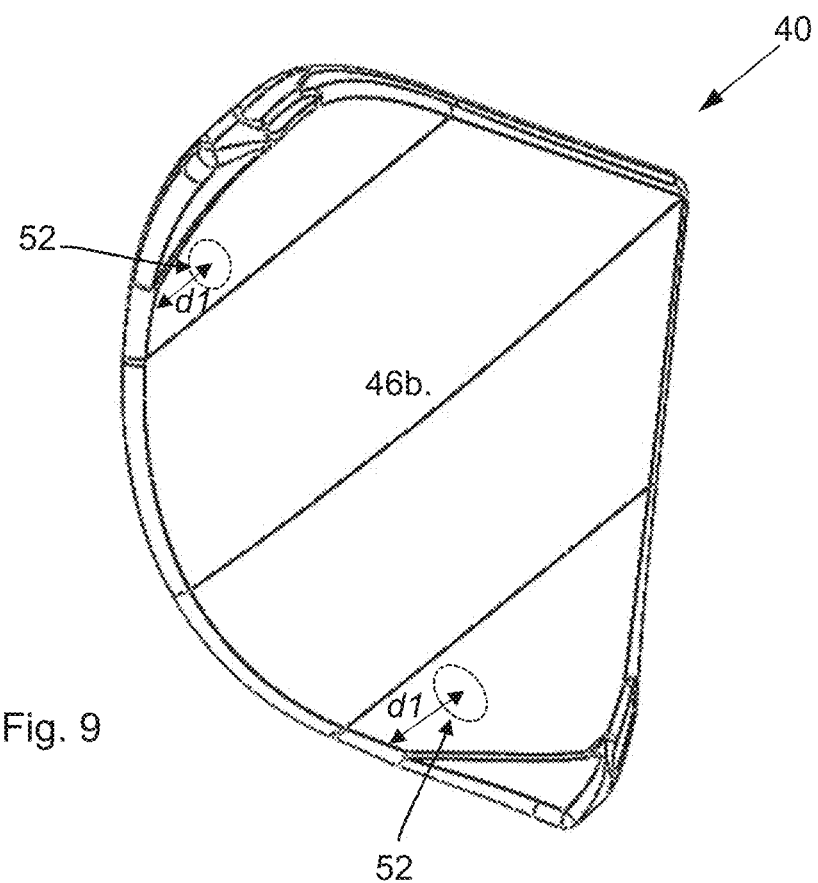
FIG. 9 illustrates a perspective view or the underside of a leaflet.
Figure 10:
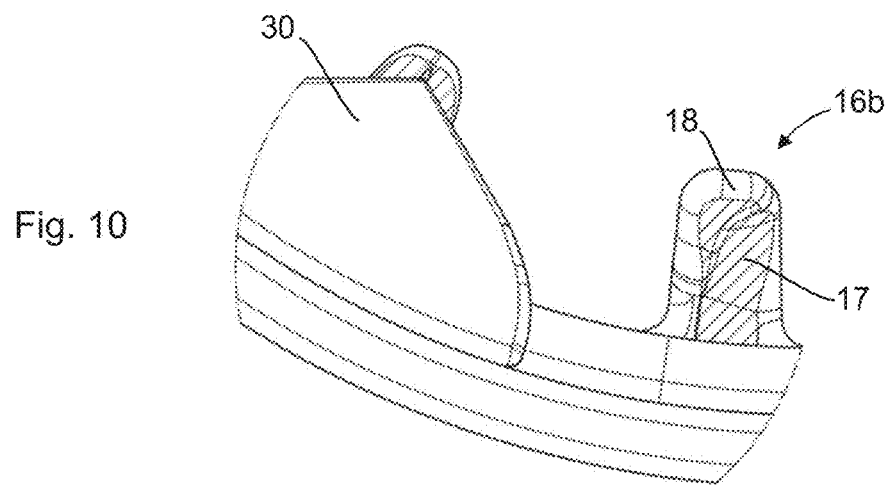
FIG. 10 illustrates an enlarged view of a portion of the annular support of FIG. 6.

In one embodiment according to FIGS. 9 and 13, the distance d1 between the center of a bearing zone 52 of each apex 18 against the internal surface 46b of the central part 46 and the leading edge 42 of each leaflet is greater than the thickness t1 of the leaflet (for example, the bearing zone 52 cannot be part of the leading edge 42 since the radius of the leading edge 42 is about half of the thickness) at the level of the center of the bearing zone 52. This distance d1 is greater than 0.5 mm and preferably greater than 1 mm, for a valve 10 having an external diameter of 19-29 mm and a leaflet thickness of less than about 1 mm (too thick leads to an increased obstruction of the flow in open position). The radii of curvature of the internal surface of the leaflet at the level of the bearing zone 52 are also greater than the thickness t1 of the leaflet at this point. In the context of the present disclosure, the radius of curvature of the internal surface of the leaflet at the bearing zone (wherein the radius of a flat surface is infinite) is defined as the smallest of the main radii. This also covers a small hole or indent in the leaflet that forms a ball-joint between the leaflet and the apex. Said otherwise, the smallest of two principal radii of curvatures of the surface of the bearing zones 52 is greater than the thickness of the leaflet at the bearing zones 52.

The heart valve 10 also comprises support members 34 arranged substantially in the middle and lower part of each guiding extension 30 (FIGS. 5 and 7) and which take the form of an element in the shape of the bow of a ship pointing upward (i.e., in the antegrade outflow direction) and profiled in the outflow direction. Each of the profiled elements 34 of the respective guiding extensions 30 comprises lateral edges that are sufficiently widely spaced to act as bearing supports for the lateral edges of the leaflets 40 when the heart valve 10 is in a closed configuration.

Furthermore, two so-called upper (i.e., on the outflow side) bearing members 20a, 20b are arranged, for each leaflet, at the level of the trailing edge 28 (FIG. 6) of the annular support 12 in a way that is axially offset along the longitudinal axis X of the annular support 12 with respect to the two lower bearing members 16a, 16b. The upper bearing members 20a, 20b are on the outflow side of the annular support (i.e., in the inflow direction), facing the external surface 46a of the leaflets 40. What is more, the two lower bearing members 16a, 16b and the two upper bearing members 20a, 20b for each leaflet may for example be offset radially with respect to one another so as to avoid the two upper bearing members 20a, 20b being placed in the wake of the two lower bearing members 16a, 16b.

With particular regard to FIGS. 16 and 17, the two upper bearing members 20a, 20b each can be elongated with a proximal end, distal end, and intermediate portion. The intermediate portion has a leading edge 21' and a trailing edge. The distal end can be a rounded apex 21 designed to come to bear against the external surface 46a of the central part 46 of each leaflet 40 throughout their pivoting about their respective axis of rotation as the heart valve 10 passes from the closed configuration to the open configuration. More particularly, each upper support apex 21 is designed to come to bear against an upper bearing zone 54 (FIG. 16) of the external surface 46a of the central part 46 of each leaflet throughout at least 20%, or else 35% or even 50% of the travel of each leaflet as the heart valve 10 passes from the closed configuration to the open configuration, something which causes the leaflet to rotate about its axis of rotation. That contact can be continuous or intermittent. When the leaflet is pushed to open by the flow, the contact is continuous during the first half of the opening.

The radii of curvature of the upper bearing zone 54 are greater than the thickness of the leaflet at this zone, as for the lower bearing zone 52, or said otherwise the smallest of two principal radii of curvatures of the surface of the upper bearing zone 54 is greater than the thickness of the leaflet at the upper bearing zone 54. As shown in FIG. 17, each apex 21 is in contact with the external surface 46a of the central part 46 of each leaflet throughout the majority of the opening travel of the leaflet, unlike in the heart valve according to WO2008152224 in which the apex of the upper bearing members is in contact with the leaflet only at the very start of the opening phase and in the zone of the leading edge of the leaflet, as illustrated in FIG. 18. The shape of the upper bearing members 20a, 20b is therefore significantly different in comparison with the shape of the upper bearing members disclosed in WO2008152224.

In particular, the two upper bearing members 20a, 20b of each leaflet are in the form of projections that extend inwardly from the internal wall 14 to overlap with the leaflets 40. The two upper bearing members 20a, 20b are inset from the downstream trailing edge 28 of the support 12. In one embodiment, the leading edge 21' of the upper bearing members 20a, 20b is substantially linear to match the external surface 46a of the leaflet. In addition, the leading edge 21', and in one embodiment the entire bearing member 20a, 20b, is inclined with respect to a plane orthogonal to the longitudinal axis X of the annular support 12, to reliably mate with the external surface 46 of the leaflet in the closed position.

As shown in FIG. 16, the leading edge 21' of the upper bearing member 20b is substantially parallel to and flush with the external surface 46a of the leaflet in the closed position. That is, in the closed configuration, the external surface 46a of the leaflet is at a predetermined angle from the leading edge 42 to the trailing edge 44 in the outflow direction A (see FIGS. 1, 2, 5). In particular, the leading edge 42 is level and the trailing edge 44 is inclined from the terminal portions 49 to the trailing point 45 in the outflow direction, such that the trailing point 45 is further extended in outflow direction than the leading edge 42 and the terminal portions 49, at the predetermined angle. In addition, the leading edge of the upper bearing member 20b is substantially at the same predetermined angle in the outflow direction as the leaflet, so that the bearing leading edge 21' is substantially parallel to and flush with the leaflet external surface 46a.

The apex 21 at the distal end of the projection is situated beyond this orthogonal plane when it coincides with the trailing edge 28 of the annular support 12. That is, the apex 21 extends outward from the downstream trailing edge 28 of the support 12 in the outflow direction. The two upper bearing members 20a, 20b each comprise a lower face (i.e., the leading edge) which is parallel to the central part 46 of the leaflets in the closed position.

Referring to FIG. 17, in the opened position, the external surface 46a of the leaflet is close to the apex 21. At the same time, the curvature at or adjacent to the leading edge 42 of the leaflet contacts the inner surface of the apex 18 of the lower bearing members 16a, 16b (also see FIG. 15). In the open position, the leaflet is in contact with the lower bearing members 16a, 16b at its leading edge 42 and at the winglet 48a with the extension 30 of the annular support on a surface adjacent to the recess 32. There is a gap with the apex 21 to avoid sticking. Those features cooperate to stop further movement of the leaflet 40 from the closed position to the opened position. The apex 21 does not engage the leading edge 42 of the leaflet 40, but is instead designed to come to bear against a bearing zone 54 (FIG. 16-54 indicates a center of the bearing zone) of the external surface 46a of the leaflet that is set back from the leading edge 42 of the leaflet by a distance d2 greater than the thickness t2 of the leaflet at the center of the bearing zone 54; thereby avoiding wear of the leading edge 42 or rotational elements.

The configuration of the upper bearing members 20a, 20b offers the advantage, over WO2008152224, that their point of contact with the leaflet is situated in a low-curvature zone of the leaflet, thus limiting the risk of wear. Another advantage is that of offering better guidance of the leaflets when the heart valve 10 passes from a closed configuration to an open configuration and of avoiding the leading edge of the leaflets coming to bear against the internal face of the annular support, leading to undesirable reaction forces. According to FIGS. 24 and 25, the reaction of the upper bearing members (only the upper bearing member 20a is visible in FIG. 22) on the leaflet 40 is exactly opposite to the opening pressure and therefore does not induce any significant reaction of the surface of revolution of the recess 32 of the extension 30 on the trailing edge 28 of the leaflet 40. The resultant force on the leaflets 40 is therefore almost zero, thereby considerably reducing the wearing of the leaflets.

By contrast, with reference to FIGS. 23, 26 and 27, the reaction at the leading edge of each leaflet, for the heart valve disclosed in WO2008152224, is not parallel to the opening pressure and induces a reaction at the trailing edge, something which may lead to premature wearing of the leaflets. It may also be appreciated from FIGS. 26 and 27 that the greater the misalignment between the opening pressure and the reaction at the leading edge, the greater will be the reaction at the trailing edge. As a result, this particular function of the upper bearing members 20a becomes all the more important the closer the leaflet is to the closed position.

In order to avoid a risk of jamming with the other members for maintaining an open position (notably the guiding surface 32 and the lower bearing members 16a, 16b), there may be a functional clearance between the upper bearing members 20a, 20b and the external face 46a of the leaflet in the open position. This arrangement also allows for a broader choice of leaflet materials, for example through the use of a material that is a little more sensitive to wear but has a density closer to that of blood, offering far less inertia during the phases of opening and closing. A material such as PEEK has a density of 1.3 whereas the pyrolytic carbon commonly employed in mechanical valve prostheses has a density of 1.7.

As depicted in FIGS. 1 and 13, the leading edge 42 of each leaflet 40 is arranged between the two lower bearing members 16a, 16b and the two upper bearing or support members 20a, 20b. It will be noted that the members for guiding the rotation of each leaflet define a virtual axis of rotation depicted in FIG. 22 and situated entirely outside of the corresponding leaflet, between the latter and the annular support 12.

In operation, at some point the heart valve 10 is in the closed position, which is best shown in FIGS. 2, 4, 5, 8, 13. The leaflets 40 come together at the trailing edges 44, and the leading edge 42 of the leaflet 40 is flush with the inner wall 14, to provide a reliable seal that prevents blood flow backward. Any blood flow in the inflow (upstream antegrade flow) direction would press the leaflets closed, and further movement is prevented at the lower bearing zone 52 by the two lower bearing members 16a, 16b, which support each leaflet 40. Specifically, the apex 18 bearing zone supports the internal surface 46b bearing zone to prevent further movement of the leaflet. The lower bearing members 16a, 16b are located between terminal portions 49a, 49b of the leaflet 40, and the lower bearing zone 52 is set inward a predetermined distance from the leaflet leading edge 42. In addition, the center support member 34 further supports the leaflet winglets 48a, 48b. Referring to FIG. 13, the leaflet leading edge 42 rests against the proximal end of the guiding surface 17. Since the lower bearing zone 52 (between the apex 18 and the internal surface 46b) is away from the leading edge 42, wear on the leading edge 42 is reduced. There is a small gap between the upper bearing members 20a, 20b and the external surface 46a of the leaflet 40, such that the upper bearing members 20a, 20b are not being utilized in the closed position.

At some point, the leaflets 40 start to move out of the closed position and toward the opened position. The force of the blood flow moves the leaflet 40 in the outflow direction. That separates the leaflet 40 from the apex 18. The leaflet 40 moves in the outflow direction A until, as shown in FIG. 16, the external surface 46a contacts the bearing leading edge of the upper bearing members 20a, 20b. At this point, turning to FIG. 17, the external surface 46a contacts the apex 21 of the upper bearing members 20a, 20b. That causes the leaflet 40 to rotate about the apex 21 at an upper bearing zone 54, with the winglets 48a, 48b guided by the recesses 32 of the guide extension 30. The upper bearing zone 54 is set back from the leading edge 42 by a predetermined distance. The trailing edges 44 of the leaflet 40 rotate to extend in the outflow direction. And the leading edge 42 rotates toward the inner surface of the lower support apex 18. Because the leaflet 40 is separated from the guiding surface 17, the leading edge 42 does not contact the guiding surface 17 during rotation, which reduces wear on the leading edge 42. The leaflets 40 are stopped when the winglets 48 contact the edge of the recesses 32, and the leaflet 40 contacts the inner surface of the lower support apex 18.

When the blood flows in the inflow direction, the blood forces the leaflets from the opened position to the closed position. The leading edge 42 of the leaflet is guided by the guiding surface 17 of the lower bearing members 16a, 16b. The motion of the leaflet stops when the internal surface 46b of the leaflet contacts the apex 18.

It is noted that in the embodiments shown, there are three leaflets 40 and three guide extensions 30. In addition, each leaflet 40 has two lower bearing members 16a, 16b and two upper bearing members 20a, 20b. Having two lower and upper bearing members 16a, 16b, 20a, 20b distributes wear and pressure more evenly across the leaflet and reduces wear on the leaflet 40. However, any suitable number of elements can be provided, including more or fewer leaflets 40 and guide extensions 30. And each leaflet can have one or more lower bearing members and/or upper bearing members.

The applicant has found that according to the valve configuration described in WO2008152224, the leading edges of the two winglets of each leaflet slide against the internal peripheral surface of the annular support as the leaflets rotate at the start of systole. Now, it has been found that constant contact between the leading edges and the internal peripheral wall of the annular support according to FIG. 20, which depicts a partial section through the mechanical prosthetic heart valve disclosed in WO2008152224 on a plane perpendicular to the longitudinal axis of the annular support, may create a flow recirculation in the obstructed zone behind the leaflets that encourages platelet aggregation and thrombus formation.

Figure 12:
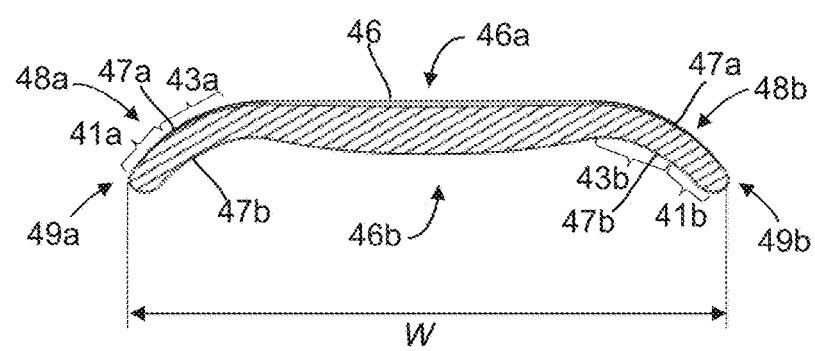
FIG. 12 illustrates a view of FIG. 11 in section on C-C.
Figure 21:
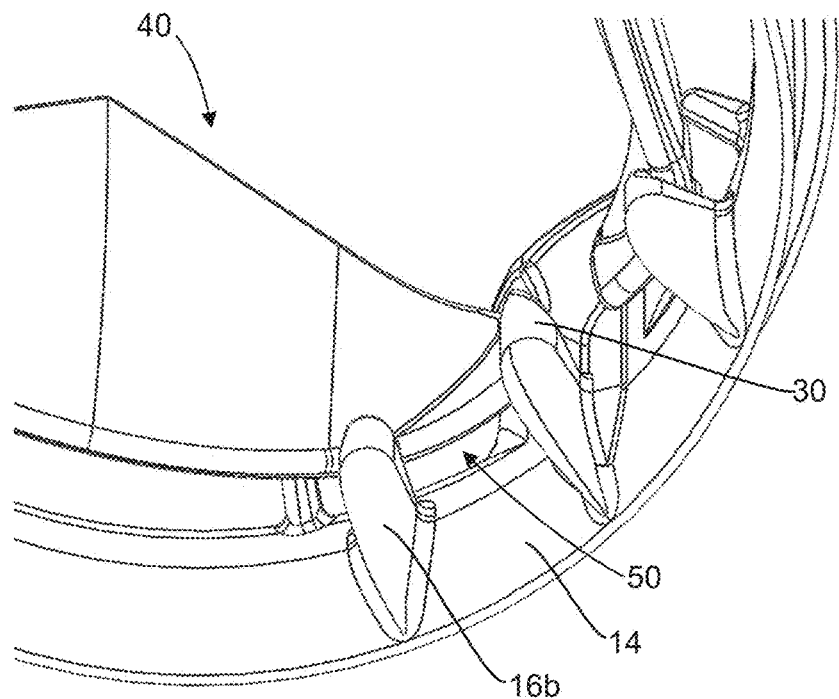
FIG. 21 illustrates a partial perspective view from underneath the mechanical prosthetic heart valve at the level of a flow channel.
Figure 22:
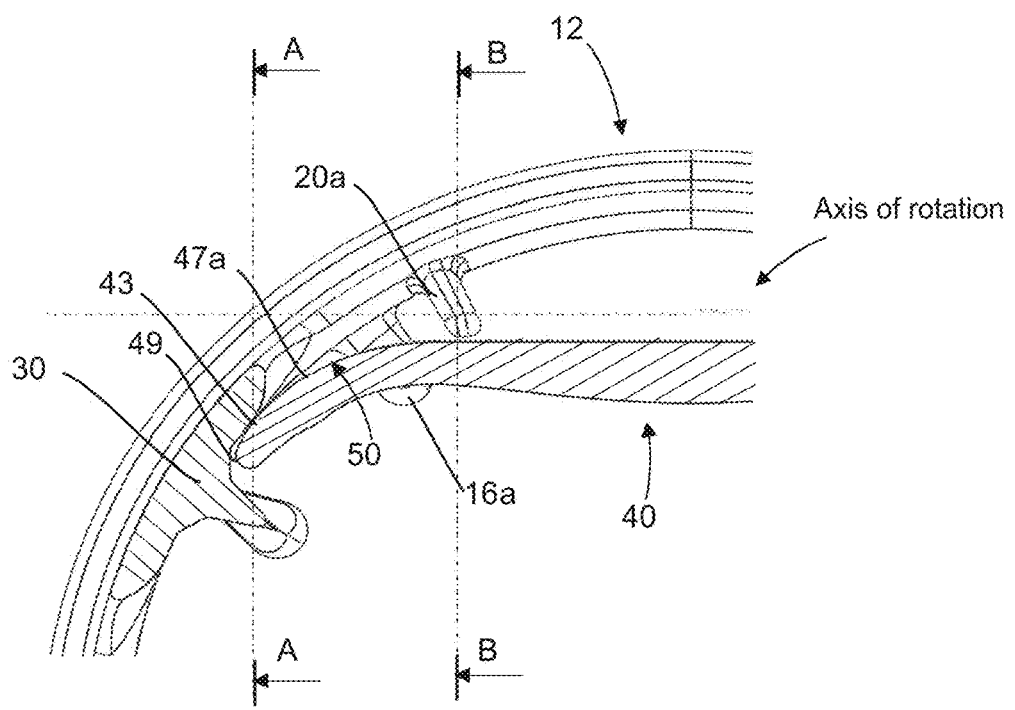
FIG. 22 illustrates a partial section through the mechanical prosthetic heart valve on a plane perpendicular to the longitudinal axis of the annular support.

According to FIGS. 11, 12 and 22, the curvature of the proximal portion 43b of the lateral winglets 48a, 48b (FIG. 12) of each leaflet 40 has been determined so that the leading edge 42 and the external face of each leaflet 40 are distant from the internal peripheral wall by at least 0.2 mm, preferably by at least 0.3 mm, or else 0.4 mm or even 0.5 mm, over at least 75% of the total width W of each leaflet and preferably over at least 80%, or else 90% when the heart valve 10 is in the open configuration. The curvature of the lateral winglets 48a, 48b of each leaflet 40 has also been determined to encourage the opening of the flow channels 50 (FIGS. 21 and 22) between the internal peripheral wall 14 of the annular support 12 and the external surface 47a of the winglets 48a, 48b of the leaflets 40.

In particular, when the leaflets are in the open position according to FIG. 1, each leaflet is in contact with the internal peripheral wall 14 of the annular support 12 only through the two end portions 49a, 49b of the leaflet as can be seen on FIG. 22. Advantageously, the contact zone of the leaflet in the open position is less than 15% of the total width W of the leaflet 40 extending between the extremities of the two terminal portions 49a, 49b (FIGS. 11 and 12), i.e. less than 7.5% at each terminal portion 49a, 49b. In a preferred embodiment, this contact zone of the leaflet is less than 10% of the width W of the leaflet 40, i.e. less than 5% at each terminal portion 49a, 49b of the leaflet, preferably less than 7.5% of the width W of the leaflet 40, i.e. less than 3.75% at each terminal portion 49a, 49b of the leaflet, and even more preferably less than 5% of the width W of the leaflet 40, i.e. less than 2.5% at each terminal portion 49a, 49b of the leaflet as illustrated in FIG. 22. In the context of the present invention, the extensions 30 of the annular support 12 are an integral part of the internal peripheral wall 14 of the support and, therefore, the leaflet contact zone at the extensions 30 must be included in the above percentages.

Furthermore, as shown in FIGS. 3, 11 and 12, the external surface 46a of each leaflet 40 in the open position is at a distance L from the internal peripherical wall 14 of the annular support 12 at least equal to 5% of the diameter of the annular support at a plane of symmetry Z of the leaflet.

As can be seen in FIG. 22, the axis of rotation of each leaflet 40 is also situated in a plane parallel to the central part 46 of the leaflet. This plane intersects the two upper bearing members 20a, 20b arranged on the internal peripheral wall 14 of the annular support 12. The axis of rotation of each leaflet is also situated at a distance from the longitudinal axis X of the annular support 12 of the heart valve 10 (in a plane perpendicular to this axis), which distance is greater than 75% of the radius of the annular support 12.

As best shown in FIG. 3, the leaflets 40 are configured in the opened position, to form a substantially triangular shape with rounded corners when arranged in the support 12. The terminal portions 49 of the leaflets 40 engage with the extensions 30, and the planar central part 46 of the leaflets 40 extend substantially linearly between the extensions 30. Accordingly, the planar central part 46 extends inwardly from the terminal portions 49 of the winglets 48 to the center of the central part 46, which is at the furthest distance to the inner wall 14 of the support 12. In addition, as best shown in FIG. 22, in the opened position, the external surface 47 of the distal end portion 41 extends substantially parallel to the inner wall 14 and contacts the recess 32.

In addition, the curved proximal end portion 43 is configured to begin at the end of the recess, so that the winglet 48 immediately turns sharply away from the inner wall 14 of the support 12, forming the gap 50 between the external surface 47 of the proximal end portion 43 and the inner wall 14 of the support 12 that forms a channel through which blood can flow. Accordingly, the distal end portion 41 extends axially outward from the extension 30, then curves inward at the curved proximal portion 43. The central part 46 extends linearly between the extensions and continues to move away from the inner wall 14 forming a larger gap between the external surface 46a of the central part 46 and inner wall 14. The channel formed by the gap 50 allows blood to more easily flow in the outflow direction. In addition, the straight central part 46 also minimizes interference with blood flow. Thus, the configuration of the leaflets 40 as arranged with the proximal portions 49 positioned at the extensions 30 and curving immediately inwardly in a linear fashion to the next neighboring extension 30, provides a widened gap 50 or channel between the leaflets 40 and the inner wall 14. In one embodiment, the distal end portion 41 can also be curved inwardly to further widen the gap 50 just to the sides of the extensions 30.

As further illustrated in FIG. 3, the center of the central part 46 is the largest distance between the leaflet 40 and the inner wall 14. The lower support or bearing members 16a, 16a are positioned at the inner wall 14 at the outermost part of the central part 46, just adjacent to the curved proximal end portion 43 of the winglet 48, to provide sufficient support as the leaflet 40 enters the closed position. The upper bearing members 20a, 20b can be positioned closer together at the central part 46.

The curvature of the proximal portion 43 of the lateral winglets 48a, 48b of each leaflet 40 and the shape and positioning of the two lower bearing members 16a, 16b makes it possible to form two flow channels 50 at the level of the terminal portions 49a, 49b of each leaflet 40 between each of the two lower bearing members 16a, 16b and one of the guiding extensions 30 of the annular support 12 when the heart valve 10 passes from a closed configuration to an open configuration. Indeed, the gap 50 between the leading edge 42 of the leaflet 40 and the trailing edge 28 of the annular support 12 are defined by the specific curvature of the leaflets, the profile of the trailing edge 28, and the shift of the axis of rotation that put the leaflet a bit more downstream with respect to the internal peripheral wall 14 in the open position. The dimensions of each flow channel 50, which is illustrated in particular in FIGS. 19, 21 and 22, increase as the leaflets 40 progressively pivot about their respective axis of rotation until such point as the heart valve 10 is in the open configuration. These flow channels have the advantage of minimizing the potential platelet aggregation zones.

By contrast, the heart valve according to WO2008152224 has no flow channels at the level of the terminal portions of each leaflet between each of the two lower bearing members and one of the guiding extensions of the annular support when the heart valve passes from a closed configuration to an open configuration, as can be seen in FIG. 23. This is mainly due to the contact zone of the leaflet, which is about 20% of the total width of the leaflet, i.e. 10% at each terminal portion of the leaflet as shown in FIG. 23. The absence of discharge channels in these critical zones may lead to an aggregation of platelets which could induce a thrombosis.

In order to manufacture the rigid-leaflets valve according to the invention, there are various materials that can be used. For the annular support, a biocompatible metal such as titanium or stellite for example is selected. It may also be possible to use solid carbon, or else a carbon coating on graphite.

The leaflets themselves are also rigid, and may be made from a biocompatible material, for example monolithic carbon, or from graphite with a coating of pyrolytic carbon. The leaflets may also be made from a biocompatible synthetic polymer which also has wear resistance properties comparable to those of pyrolytic carbon. Thus, a material such as "PEEK" (which stands for polyetheretherketone) has a low density of the order of 1.3 and is particularly suitable for the manufacture of the leaflets. This material may be reinforced with carbon in order to increase the wear resistance of the leaflets.

It will be noted that the valve according to the invention can be made of titanium in the case of the annular support 12 and of PEEK for the leaflets, something which affords a pairing of materials that is perfectly suited to the rubbing and wearing encountered in this type of valve. Furthermore, PEEK can also be used as a material for manufacturing the leaflets and pyrolytic carbon for the support, or even pyrolytic carbon for the leaflets and the support.

It is further noted that the drawings may illustrate and the description and claims may use several geometric or relational terms and directional or positioning terms, such as profiled, square, rectangular, triangular, linear, curved, curvature, rounded, parallel, perpendicular, orthogonal, transverse, axially, circular, flat, leading, trailing, forward, upper, lower, up, down, inner, outer, internal, external, side, distal, and proximal. Those terms are merely for convenience to facilitate the description based on the embodiments shown in the figures, and are not intended to limit the invention. Thus, it should be recognized that the invention can be described in other ways without those geometric, relational, directional or positioning terms. In addition, the geometric or relational terms may not be exact. For instance, walls or surfaces may not be exactly flat, perpendicular or parallel to one another but still be considered to be substantially perpendicular or parallel because of, for example, roughness of surfaces, tolerances allowed in manufacturing, etc. And, other suitable geometries and relationships can be provided without departing from the scope of the appended claims.

It will be apparent to those skilled in the art having the benefit of the teachings presented in the foregoing descriptions and the associated drawings that modifications, combinations, sub-combinations, and variations can be made without departing from the spirit or scope of this disclosure. Likewise, the various examples described may be used individually or in combination with other examples. Those skilled in the art will appreciate various combinations of examples not specifically described or illustrated herein that are still within the scope of this disclosure. In this respect, it is to be understood that the disclosure is not limited to the specific examples set forth and the examples of the disclosure are intended to be illustrative, not limiting.

LIST OF REFERENCES

Mechanical prosthetic heart valve 10
Annular support 12
Internal peripheral wall 14
Lower bearing members 16a, 16b
Support body 19
Proximal end 19a
Guiding surface 17
Apex 18
Upper bearing members 20a, 20b
Apex 21
Leading edge 21'
Exterior peripheral wall 22
Peripheral rib 24
Leading edge 26
Trailing edge 28
Guiding extensions 30
Profiled recess 32
Guiding arc
Bearing members 34
Mobile leaflets 40
Leading edge 42
Trailing edge 44
Symmetrical portions 44a, 44b
Tip 45
Central part 46
External surface 46a
Internal surface 46b
Lateral winglets 48a, 48b
Distal end portions 41a, 41b Proximal end portions 43a, 43b
External surface 47a
Internal surface 47b
Terminal portions 49a, 49b
Flow channel 50
Lower bearing zones 52
Upper bearing zones 54

The invention claimed is:

1. A mechanical prosthetic heart valve comprising:
an annular support comprising an internal peripheral wall centered about a longitudinal axis and delimiting an internal passage,
at least two mobile leaflets arranged in such a way as to each be able to effect a rotational movement about an axis of rotation perpendicular to said longitudinal axis so that the valve can pass from a closed configuration to an open configuration and vice versa, the leaflets between them delimiting a main orifice centered on the longitudinal axis and through which the blood can flow axially when the valve is in the open configuration, the leaflets at least partially obstructing the internal passage of the annular support so as to be able to prevent the blood from flowing back through the main orifice when the valve is in the closed configuration,
each leaflet comprising a leading edge designed to come against a portion of the internal peripheral wall of the annular support when the valve is in the closed configuration, an internal surface extending from the leading edge, an external surface opposite the internal surface and extending from the leading edge, and two terminal portions,
the annular support comprising two opposite edges and as many extensions as the number of leaflets, which extend axially from one of the opposite edges, a profiled recess being created on two opposite sides of each extension, the recesses acting as guide surfaces for the respective terminal portions of each leaflet as the valve passes from an open configuration to a closed configuration, and vice versa, the annular support further comprising, on the internal peripheral wall, two lower bearing members per leaflet which are situated between two of said extensions and designed to be in abutment against the corresponding leaflet when the valve is in a closed configuration,
wherein a contact zone of each leaflet in the open position with the internal peripheral wall of the annular support within a plane perpendicular to the longitudinal axis of the annular support is less than 15% of a total width of each leaflet extending along a straight line between the extremities of the two terminal portions; and
wherein the leading edge and the external surface of each leaflet are distant by at least 0.2 mm from the internal peripheral wall over at least 75% of the distance of the leading edge separating the two terminal portions of each leaflet when the heart valve is in the open configuration.

2. The mechanical prosthetic heart valve of claim 1, wherein a contact zone of each leaflet in the open position with the internal peripheral wall is less than 10% of said total width of the leaflet.

3. The mechanical prosthetic heart valve of claim 1, wherein a contact zone of each leaflet in the open position with the internal peripheral wall is less than 7.5% of said total width of the leaflet.

4. The mechanical prosthetic heart valve of claim 1, wherein a contact zone of each leaflet in the open position with the internal peripheral wall is less than 5% of said total width of the leaflet.

5. The mechanical prosthetic heart valve of claim 1, wherein each leaflet comprises a central part and two lateral winglets flanking the central part symmetrically with respect to a plane of symmetry of the leaflet, each lateral winglet comprising an external surface, an internal surface and one of the two terminal portions, two flow channels being located at the level of the terminal portions of each leaflet between each of the two lower bearing members and one of the extensions of the annular support when the heart valve is in the open configuration.

6. The mechanical prosthetic heart valve of claim 5, wherein said two flow channels are delimited by the internal peripheral wall of the annular support and the external surface of the respective two lateral winglets.

7. The mechanical prosthetic heart valve of claim 5, wherein the lateral winglets are inclined with respect to the central part of each leaflet, said lateral winglets having a respective first and second curved proximal end portion extending from the central part with a curved external surface and a respective first and second distal end portion contacting respectively one and another extensions of the annular support when the heart valve is in the open configuration, wherein the first and second distal end portions extend parallel to the internal peripheral wall and are aligned with respectively the one and another extensions, and wherein the curved external surface of each of the first and second proximal portions curves away from the internal peripheral wall outside respectively said one and another extensions in the open configuration.

8. The mechanical prosthetic heart valve of claim 5, wherein the two flow channels form right from the start of pivoting of each leaflet as the heart valve passes from a closed configuration to an open configuration, the dimensions of the two flow channels which are associated with each leaflet increasing as the leaflets progressively pivot until such point as the valve is in the open configuration.

9. The mechanical prosthetic heart valve of claim 1, wherein the surface of said internal peripheral wall of the annular support is a continuous surface devoid of windows at the level of the end portions of each leaflet.

10. A mechanical prosthetic heart valve comprising:
an annular support comprising an internal peripheral wall centered about a longitudinal axis and delimiting an internal passage,
at least two mobile leaflets arranged in such a way as to each be able to effect a rotational movement about an axis of rotation perpendicular to said longitudinal axis so that the valve can pass from a closed configuration to an open configuration and vice versa, the leaflets between them delimiting a main orifice centered on the longitudinal axis and through which the blood can flow axially when the valve is in the open configuration, the leaflets at least partially obstructing the internal passage of the annular support so as to be able to prevent the blood from flowing back through the main orifice when the valve is in the closed configuration,
each leaflet comprising a leading edge designed to come against a portion of the internal peripheral wall of the annular support when the valve is in the closed configuration, an internal surface extending from the leading edge, an external surface opposite the internal surface and extending from the leading edge, and two terminal portions, the annular support comprising two opposite edges and as many extensions as the number of leaflets, which extend axially from one of the opposite edges, a profiled recess being created on two opposite sides of each extension, the recesses acting as guide surfaces for the respective terminal portions of each leaflet as the valve passes from an open configuration to a closed configuration, and vice versa, the annular support further comprising, on the internal peripheral wall, two lower bearing members per leaflet which are situated between two of said extensions and designed to be in abutment against the corresponding leaflet when the valve is in a closed configuration, wherein a contact zone of each leaflet in the open position with the internal peripheral wall of the annular support within a plane perpendicular to the longitudinal axis of the annular support is less than 15% of a total width of each leaflet extending along a straight line between the extremities of the two terminal portions, and wherein the leading edge and the external surface of each leaflet are distant by at least 0.5 mm from the internal peripheral wall over at least 75% of the distance of the leading edge separating the two terminal portions of each leaflet when the heart valve is in the open configuration.

11. A mechanical prosthetic heart valve comprising:

an annular support comprising an internal peripheral wall centered about a longitudinal axis and delimiting an internal passage, at least two mobile leaflets arranged in such a way as to each be able to effect a rotational movement about an axis of rotation perpendicular to said longitudinal axis so that the valve can pass from a closed configuration to an open configuration and vice versa, the leaflets between them delimiting a main orifice centered on the longitudinal axis and through which the blood can flow axially when the valve is in the open configuration, the leaflets at least partially obstructing the internal passage of the annular support so as to be able to prevent the blood from flowing back through the main orifice when the valve is in the closed configuration, each leaflet comprising a leading edge designed to come against a portion of the internal peripheral wall of the annular support when the valve is in the closed configuration, an internal surface extending from the leading edge, an external surface opposite the internal surface and extending from the leading edge, and two terminal portions, the annular support comprising two opposite edges and as many extensions as the number of leaflets, which extend axially from one of the opposite edges, a profiled recess being created on two opposite sides of each extension, the recesses acting as guide surfaces for the respective terminal portions of each leaflet as the valve passes from an open configuration to a closed configuration, and vice versa, the annular support further comprising, on the internal peripheral wall, two lower bearing members per leaflet which are situated between two of said extensions and designed to be in abutment against the corresponding leaflet when the valve is in a closed configuration, wherein a contact zone of each leaflet in the open position with the internal peripheral wall of the annular support within a plane perpendicular to the longitudinal axis of the annular support is less than 15% of a total width of each leaflet extending along a straight line between the extremities of the two terminal portions, and wherein the leading edge and the external surface of each leaflet are distant by at least 0.5 mm from the internal peripheral wall over at least 90% of the distance of the leading edge separating the two terminal portions of each leaflet when the heart valve is in the open configuration.

12. The mechanical prosthetic heart valve of claim 1, wherein, in a plane perpendicular to the longitudinal axis of the valve, the axis of rotation of each leaflet is situated at a distance from the longitudinal axis that is greater than 75% of the radius of the annular support.

13. The mechanical prosthetic heart valve of claim 1, wherein the distance between the axis of rotation of each leaflet and the external surface of a central part of the leaflet is greater than 0.2 mm.

14. The mechanical prosthetic heart valve of claim 1, wherein the external surface of each leaflet in the open position is at a distance from the internal peripherical wall of the annular support at least equal to 5% of the diameter of said annular support at a plane of symmetry of the leaflet.

15. The mechanical prosthetic heart valve of claim 1, wherein the at least two mobile leaflets comprise three leaflets pivotally mounted between three extensions, wherein six flow channels are formed when the valve is in the open configuration, said flow channels being located adjacent to each lateral side of each extension.

16. A mechanical prosthetic heart valve comprising:

an annular support comprising an internal peripheral wall centered about a longitudinal axis and delimiting an internal passage, at least two mobile leaflets arranged in such a way as to each be able to effect a rotational movement about an axis of rotation perpendicular to said longitudinal axis so that the valve can pass from a closed configuration to an open configuration and vice versa, the leaflets between them delimiting a main orifice centered on the longitudinal axis and through which the blood can flow axially when the valve is in the open configuration, the leaflets at least partially obstructing the internal passage of the annular support so as to be able to prevent blood from flowing back through the main orifice when the valve is in the closed configuration, each leaflet comprising a leading edge designed to come against a portion of the internal peripheral wall of the annular support when the valve is in the closed configuration, an internal surface extending from the leading edge, an external surface opposite the internal surface and extending from the leading edge, and two terminal portions, the annular support comprising two opposite edges and as many extensions as the number of leaflets, which extend axially from one of the opposite edges, a profiled recess being created on two opposite sides of each extension, the recesses acting as guide surfaces for the respective terminal portions of each leaflet as the valve passes from an open configuration to a closed configuration, and vice versa, the annular support further comprising, on the internal peripheral wall, two lower bearing members per leaflet which are situated between two of said extensions and designed to be in abutment against the corresponding leaflet when the valve is in a closed configuration, wherein a contact zone of each leaflet in the open position with the internal peripheral wall is less than 15% of a total width of each leaflet extending between the extremities of the two terminal portions and wherein the leading edge and the external surface of each leaflet are distant by at least 0.2 mm from the internal peripheral wall over at least 75% of the distance of the leading edge separating the two terminal portions of each leaflet when the heart valve is in the open configuration.

17. The mechanical prosthetic heart valve of claim 16, wherein the leading edge and the external surface of each leaflet are distant by at least 0.5 mm from the internal peripheral wall over at least 75% of the distance of the leading edge separating the two terminal portions of each leaflet when the heart valve is in the open configuration.

18. The mechanical prosthetic heart valve of claim 16, wherein the leading edge and the external surface of each leaflet are distant by at least 0.5 mm from the internal peripheral wall over at least 90% of the distance of the leading edge separating the two terminal portions of each leaflet when the heart valve is in the open configuration.

\* \* \* \* \*